US007749506B2

(12) United States Patent
van Hulten et al.

(10) Patent No.: US 7,749,506 B2
(45) Date of Patent: Jul. 6, 2010

(54) PROTEINS DERIVED FROM WHITE SPOT SYNDROME VIRUS AND USES THEREOF

(75) Inventors: Maria Cornelia Wilhelmina van Hulten, Wageningen (NL); Justinus Maria Vlak, Rhenen (NL)

(73) Assignee: Intervet International B.V., Boxmeer (NL)

( * ) Notice: Subject to any disclaimer, the term of this patent is extended or adjusted under 35 U.S.C. 154(b) by 357 days.

(21) Appl. No.: 11/737,227

(22) Filed: Apr. 19, 2007

(65) Prior Publication Data

US 2009/0068212 A1 Mar. 12, 2009

Related U.S. Application Data

(63) Continuation of application No. 10/048,749, filed as application No. PCT/EP00/07290 on Jul. 26, 2000, now abandoned.

(30) Foreign Application Priority Data

Aug. 3, 1999 (EP) ................................ 99202545
Jan. 24, 2000 (EP) ................................ 00200248

(51) Int. Cl.
*A61K 39/12* (2006.01)
*C07K 14/00* (2006.01)
*C12P 21/04* (2006.01)
*C07H 21/04* (2006.01)

(52) U.S. Cl. ................ 424/186.1; 424/184.1; 530/300; 530/350; 435/69.1; 435/69.5; 435/69.7; 536/23.5; 536/23.7

(58) Field of Classification Search ....................... None
See application file for complete search history.

(56) References Cited

FOREIGN PATENT DOCUMENTS

| | | |
|---|---|---|
| EP | 0785255 A2 | 7/1997 |
| EP | 0785255 A3 | 10/1998 |
| EP | 0785255 B1 | 9/2004 |

OTHER PUBLICATIONS

Nadala et al 1998, Diseases of Aquatic Organisms, 33, 231-234.*
Altschul, S.F. et al. (1997). Gapped BLAST and PSI-BLAST: a new generation of protein database search programs. Nucleic Acids Research. 25(17):3389-3402.

Durand, S. et al. (1997). Ultrastructure and morphogenesis of White Spot Syndrome Baculovirus (WSSV). Diseases of Aquatic Organisms. 29:205-211 .

Flegel, T.W. (1997). Special topic review: Major viral diseases of the black tiger prawn (*Penaeus monodon*) in Thailand. World Journal of Microbiology & Biotechnology. 13:433-442.
Garnier, J. (1978). Analysis of the Accuracy and Implications of Simple Methods for Predicting the Secondary Structure of Globular Proteins. Journal Molecular Biology. 120:97-120.
Hansen, J.E. et al. (1998). NetOglyc: Prediction of mucin type O-glycosylation sites based on sequence context and surface accessibility. Glycoconjugate Journal. 15:115-130.
Kozak, M. (1989). The Scanning Model for Translation: An Update. The Journal of Cell Biology. 108:229-241.
Pearson, W. R. et al. (1988). Improved Tools for Biological Sequence Comparison. Proceedings of the National Academy of Sciences. 85(8):2444-2448.
Reilander, H. et al. (1996). Functional Expression of the *Aequorea victoria* Green Fluorescent Protein in Insect Cells Using the Baculovirus Expression System. Biochemical and Biophysical Research Communications. 219 (1):14-20.
Rodriguez, J. et al. (1995). Characterisation of shrimp haemocytes and plasma components by monoclonal antibodies. Journal of Cell Science. 108:1043-1050.
Smith, G.E. et al. (1978). Analysis of Baculovirus Genomes with Restriction Endonucleases. Virology. 89:517-527.
Sonnhammer, E.L.L. et al. (1998). A hidden Markov model for predicting transmembrane helices in protein sequences. In Journal Glasgow et al., eds., Proc. Sixth Int. Conf. on Intelligent Systems for Molecular Biology. 175-182. AAAI Press.
van Hulten M.C.W. et al. (2000). Analysis of a genomic segment of white spot syndrome virus of shrimp containing ribonucleotide reductase genes and repeat regions. Journal of General Virology. 81:307-316.
Vaughn, J.L. et al. (1977). The establishment of two cell lines from the insect *Spodoptera frugiperda* (Lepidoptera; Noctuidae). In Vitro. 13(4):213-217.
Wongteerasupaya, C. et al. (1995). A non-occluded, systemic baculovirus that occurs in cells of ectodermal and mesodermal origin and causes high mortality in the black tiger prawn *Penaeus monodon*. Diseases of Aquatic Organisms. 21:69-77.
Yang, F. et al. (1997). A simple and efficient method for purification of prawn baculovirus DNA. Journal of Virological Methods. 67:1-4.
Lo, Chu-Fang et al. (1999). Specific genomic DNA fragment analysis of different geographical clinical samples of shrimp white spot syndrome virus. Diseases of Aquatic Organisms. 35:175-185.
Van Hulten, M.C.W. et al. (2000). Identification of two major virion protein genes of white spot syndrome virus of shrimp. Virology. 266:227-236.
Nadala, E.C.B. et al. (Jul. 30, 1998). A comparative study of three different isolates of white spot virus. Diseases of Aquatic Organisms. 33:231-234.
Witteveldt, J. et al. (Feb. 2004). Protection of *Penaeus monodon* against white spot syndrome virus by oral vaccination. Journal of Virology. 78:4, pp. 2057-2061.

Witteveldt, J. et al. (2004). Protection of *Penaeus monodon* against white spot syndrome virus using a WSSV subunit vaccine. Fish & Shellfish Immunology. 16:571-579.

Magbanua, F. O. et al. (2000). White spot syndrome virus (WSSV) in cultured *Penaeus monodon* in the Philippines. Diseases of Aquatic Organisms. 42:77-82.

* cited by examiner

*Primary Examiner*—Robert B Mondesi
*Assistant Examiner*—Padma V Baskar
(74) *Attorney, Agent, or Firm*—William M. Blackstone

(57) ABSTRACT

Embodiments of the present invention generally relate to proteins derived from white spot syndrome virus, nucleic acid sequences encoding them, and their use in the manufacture of a vaccine for prophylaxis and/or treatment of white spot syndrome in crustaceans.

4 Claims, 12 Drawing Sheets

Figure 2b

```
GGATCCAACCAACACGTAAAGGAAGAACTTCCATCTAAAACAAAGAAAAATGGAATTTGGCAACCTAACA
                                                  M  E  F  G  N  L  T
AACCTGGACGTTGCAATTATTGCAATCTTGTCCATTGCAATCATTGCTCTAATCGTTATCATGGTTATAA
 N  L  D  V  A  I  I  A  I  L  S  I  A  I  I  A  L  I  V  I  M  V  I  M
TGATTGTATTCAACACACGTGTTGGAAGAAGCGTCGTCGCTAATTATGATCAGATGATGCGAGTCCCAAT
 I  V  F  N  T  R  V  G  R  S  V  V  A  N  Y  D  Q  M  M  R  V  P  I
TCAAAGAAGGGCAAAGGTAATGTCAATTCGTGGAGAGAGGTCCTACAATACTCCTCTTGGAAAGGTGGCC
 Q  R  R  A  K  V  M  S  I  R  G  E  R  S  Y  N  T  P  L  G  K  V  A
ATGAAGAATGGTCTCTCCGATAAGGACATGAAGGATGTTTCTGCTGATCTTGTCATCTCTACCGTCACAG
 M  K  N  G  L  S  D  K  D  M  K  D  V  S  A  D  L  V  I  S  T  V  T  A
CCCCAAGGACTGATCCCGCTGGCACTGGGGCCGAGAACTCTAACATGACTTTGAAGATCCTCAACAACAC
 P  R  T  D  P  A  G  T  G  A  E  N  S  N  M  T  L  K  I  L  N  N  T
TGGCGTCGATCTCTTGATCAACGACATTACTGTTCGGCCAACTGTTATTGCAGGAAACATTAAGGGAAAT
 G  V  D  L  L  I  N  D  I  T  V  R  P  T  V  I  A  G  N  I  K  G  N
ACTATGTCGAACACTTACTTCTCGAGCAAGGACATTAAATCTTCATCTTCAAAAATTACCCTCATTGACG
 T  M  S  N  T  Y  F  S  S  K  D  I  K  S  S  S  K  I  T  L  I  D  V
TGTGCAGCAAATTTGAAGACGCGCAGCCTTCGAAGCTACAATGAACATTGGATTCACCTCCAAGAATGTG
 C  S  K  F  E  D  A  Q  P  S  K  L  Q  *
ATCGATATCAAGGACGAAATCAAGAAGAAGTAAAGTGGGAATTGTACAAATATAAAGGTTTTGTTTGAAT
                                                                  ---
AAAAATACAAGTAATTTTATACCATCTTTTATTTTTCTAATCCTTTGAAATGTATCTTGTTACCTGACTC
---polyA
ATTACAAATTTCTCATCATCCCTAAAGAATGTGTACAAATCATCATTAGCAAATGTACAAATAAAGTTAG
TCAAAAACACACAAATATTAATCTTCATGTTGTAAGGAATGTTGGACACAACAGTACCCAGAACACTGTT
```

Figure 2c

```
AATGCAACCACCCAAGAGAGCAAAACTTCTTCCCCAACAATCTCCTCGACCCCAACTACATATTCTGGCA
GCTCAACCAGCAGGGGTCCAGGTTCTGGATCTGGAAACAAACCCAAAGATGACACATCCGTTGAAGGAAT
AGACCCTGGCTTACTGTAACAGAAAAAAGAGTAAAAGGCGACAGCTCGCTTGCCAATTGTCCTGTTACGT
ACTCTGTGGTTTCACGAGGTTGTCATCACCAAAGGTAACCTTTTTTTTTGTCCTCGCCGACAAAACGACA
TCTTAATAACCAAGCAACGTTCGATAAAGAAAAAAACTCGTCATGGATCTTTCTTTCACTCTTTCGGTCG
                                         M  D  L  S  F  T  L  S  V  V
TGTCGGCCATCCTCGCCATCACTGCTGTGATTGCTGTATTTATTGTGATTTTTAGGTATCACAACACTGT
 S  A  I  L  A  I  T  A  V  I  A  V  F  I  V  I  F  R  Y  H  N  T  V
GACCAAGACCATCGAAACCCACACAGACAATATCGAGACAAACATGGATGAAAACCTCCGCATTCCTGTG
 T  K  T  I  E  T  H  T  D  N  I  E  T  N  M  D  E  N  L  R  I  P  V
ACTGCTGAGGTTGGATCAGGCTACTTCAAGATGACTGATGTGTCCTTTGACAGCGACACCTTGGGCAAAA
 T  A  E  V  G  S  G  Y  F  K  M  T  D  V  S  F  D  S  D  T  L  G  K  I
TCAAGATCCGCAATGGAAAGTCTGATGCACAGATGAAGGAAGAAGATGCGGATCTTGTCATCACTCCCGT
  K  I  R  N  G  K  S  D  A  Q  M  K  E  E  D  A  D  L  V  I  T  P  V
GGAGGGCCGAGCACTCGAAGTGACTGTGGGGCAGAATCTCACCTTTGAGGGAACATTCAAGGTGTGGAAC
 E  G  R  A  L  E  V  T  V  G  Q  N  L  T  F  E  G  T  F  K  V  W  N
AACACATCAAGAAAGATCAACATCACTGGTATGCAGATGGTGCCAAAGATTAACCCATCAAAGGCCTTTG
 N  T  S  R  K  I  N  I  T  G  M  Q  M  V  P  K  I  N  P  S  K  A  F  V
TCGGTAGCTCCAACACCTCCTCCTTCACCCCCGTCTCTATTGATGAGGATGAAGTTGGCACCTTTGTGTG
  G  S  S  N  T  S  S  F  T  P  V  S  I  D  E  D  E  V  G  T  F  V  C
TGGTACCACCTTTGGCGCACCAATTGCAGCTACCGCCGGTGGAAATCTTTTCGACATGTACGTGCACGTC
 G  T  T  F  G  A  P  I  A  A  T  A  G  G  N  L  F  D  M  Y  V  H  V
ACCTACTCTGGCACTGAGACCGAGTAAATAAATCGTGCTTTTTTATATAGATAGGGAATTTTAATATTAC
 T  Y  S  G  T  E  T  E  *
AACAATAAGAAAATAAAACAATTGAGGAAATTTATACCATATTTTATTGACCTACTTAACCTTCTTGCTA
             ------polyA
TACAATGAATGTTTAAGTGACTGGAAAAGTTTAGCAATATTATCCTTGAACGGGAAACATGCACCAATTA
```

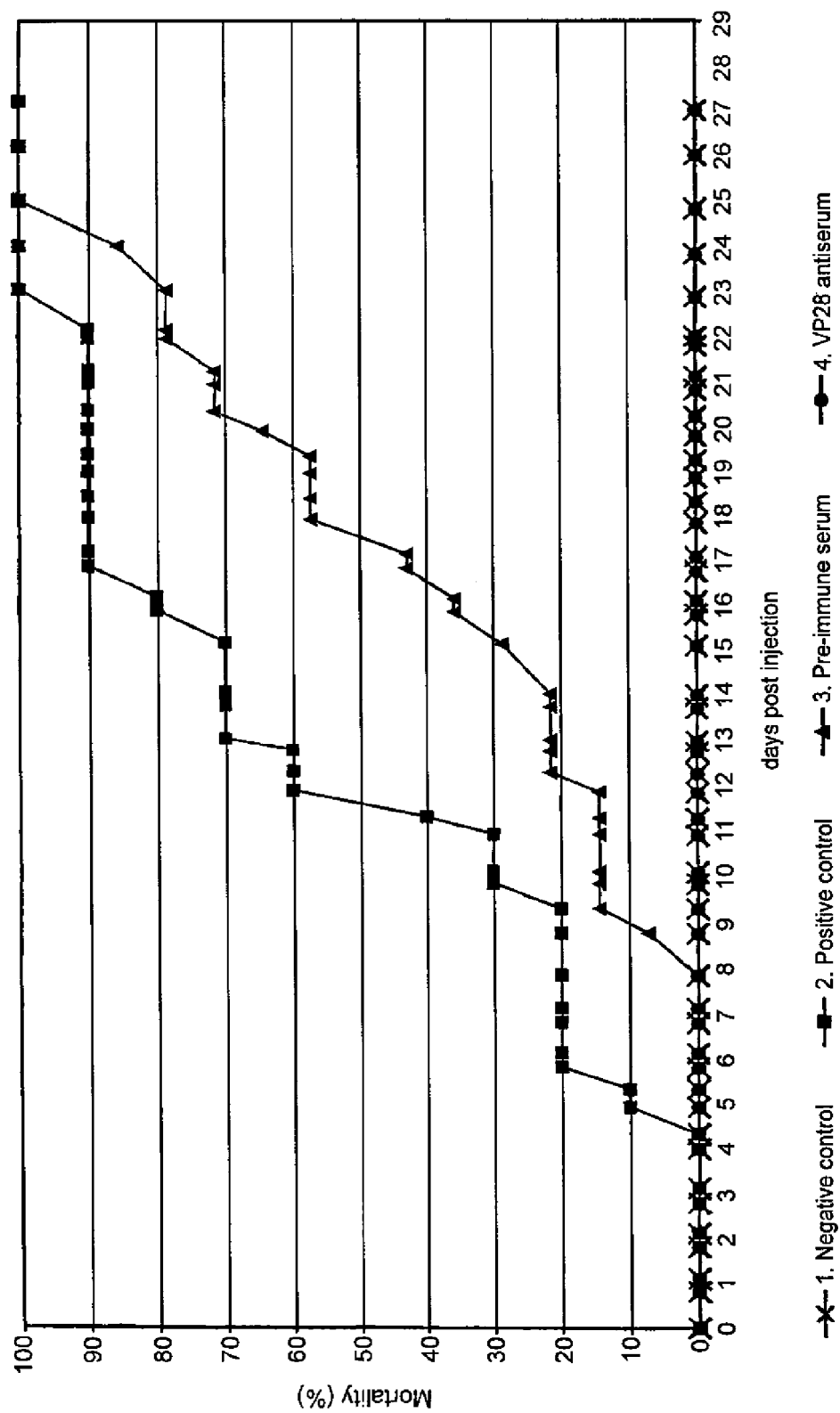

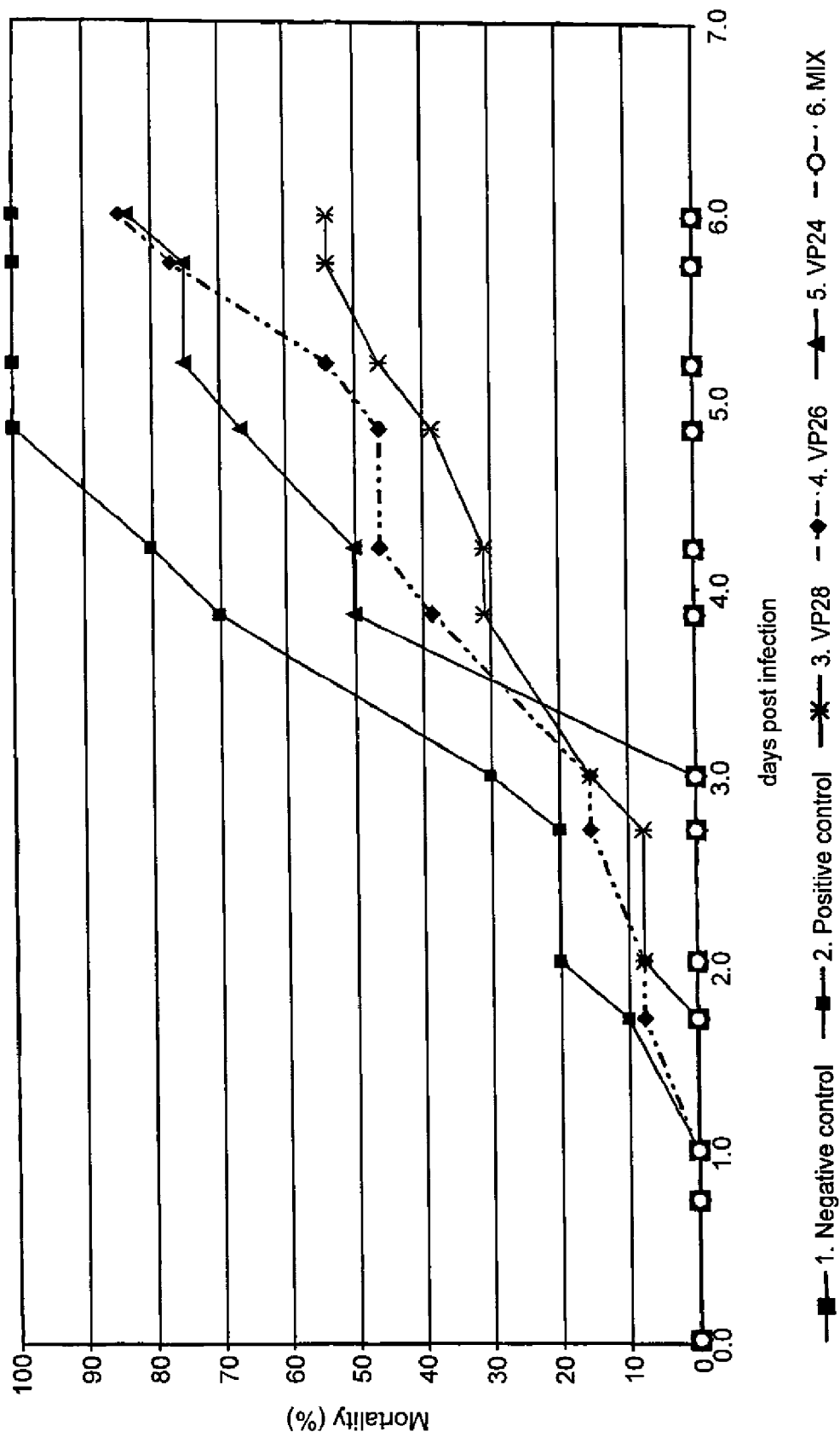

US 7,749,506 B2

PROTEINS DERIVED FROM WHITE SPOT SYNDROME VIRUS AND USES THEREOF

PRIORITY CLAIM TO RELATED PATENT APPLICATIONS

This application is a continuation of U.S. application Ser. No. 10/048,749, filed on Jan. 31, 2002, now abandoned, incorporated herein by reference. This patent claims priority under 35 U.S.C. §371 as a national phase of International Patent Application No. PCT/EP00/07290 (filed Jul. 26, 2000; and published on Feb. 8, 2001 as International Publication No. WO 01/09340), which, in turn, claims priority to European Patent Application Nos. 99202545.2 (filed Aug. 3, 1999) and 00200248.3 (filed Jan. 24, 2000), all of which are incorporated herein by reference.

REFERENCE TO SEQUENCE LISTING

The material saved as "text document" under the file name "Sequence Listing" created on May 21, 2008, is hereby incorporated by reference.

BACKGROUND OF THE INVENTION

White Spot Syndrome Virus (WSSV) is a major viral disease in shrimp in large areas of Southeast Asia. The virus has a wide host range among crustaceans (Flegel, 1997) and there is little genetic variation among isolates (Lo et al, 1999). Electron microscopy (EM) studies showed that the virions are enveloped and have a rod to bullet shaped appearance of about 275 nm in length and 120 nm wide with a tail-like appendage at one end. Nucleocapsids, which have lost their envelope, have a crosshatched appearance and a size of about 300 nm×70 nm (Wongteerasupaya et al., 1995). This virion morphology, its nuclear localization and its morphogenesis are reminiscent of baculoviruses in insects (Durand et al., 1997). Originally, WSSV has been classified as an unassigned member of the Baculoviridae family (Francki et al., 1991) hence the virus has been referred to as Systemic Ectodermal Mesodermal Baculo virus (SEMBV) or White Spot Baculo virus (WSBV). At present WSSV is no longer accepted into this family (Murphy et al., 1995) due to lack of molecular information. The double stranded viral DNA has a size of well over 200 kb as derived from restriction endonuclease analysis (Yang et al., 1997).

An outbreak of WSSV in cultured shrimp in Southeast Asia causes mass mortality among the shrimp. The disease is characterized by white spots on the carapace, appendages and cutucie and reddish coloration of the hepatopancreas of the shrimp. The infected shrimps show signs of lethargy and a rapid reduction in food consumption and within 3 to 5 days these shrimp normally die. An outbreak of WSSV leads to heavy losses in the industry of cultured shrimp and as a consequence there is a strong need for vaccines that can protect against WSSV infections. The identification and characterization of major structural WSSV proteins that can be used in such a vaccine would provide the means to develop such vaccines.

Four major proteins of WSSV have been identified which have been designated VP28 (28 kDa), VP26 (26 kDa), VP24 (24 kDa) and VP19 (19 kDa due to their molecular weight estimated from their mobility in Coomassie Brilliant Blue-stained SDS-PAGE gels. VP26 and VP24 are nucleocapsid proteins, whereas VP28 and Vp19 are envelope proteins. The N-terminal amino acid residues of the WSSV proteins were obtained by protein sequencing, and were used to identify their genes (vp28, vp26, vp24, vp19, respectively) on the WSSV genome. The open reading frame (ORF) of vp26 comprises 555 nucleotides and is depicted in FIG. 2b (SEQ ID NO. 1) together with the deduced amino acid sequence of VP26, which is depicted as an 184 amino acid residues sequence (SEQ ID NO. 3) in FIG. 2b. A second open reading frame of vp26 comprises 612 nucleotides and is depicted in SEQ ID NO. 9 together with the deduced amino acid sequence consisting of 204 residues, which is separately depicted as SEQ ID NO. 10. The open reading frame of vp28 comprises 615 nucleotides (SEQ ID NO. 2) and is depicted in FIG. 2c together with the deduced amino acid sequence (SEQ ID NO. 4). The deduced amino acid sequence of VP28 is 204 amino acids. Both VP26 and VP28 contain a putative transmembrane domain at the N-terminus and many putative N- and O-glycosylation sites. The ORF of the genes vp26 and vp28 coded for proteins with a theoretical size of 20 kDa and 22 kDa respectively. The theoretical amino acid sequence of VP26 and VP28 was confirmed by direct protein sequencing. The theoretical sizes of VP26 and VP28 differ 6 kDa from the size estimated by their mobility in Coomassie Brilliant Blue-stained SDS-PAGE gels. This size difference could be explained by posttranslational modifications such as glycosylation, phosphorylation, etc. The N-terminal amino acid sequence of VP24 and the partial amino acid sequence of VP19 are depicted in SEQ ID NOS. 5 and 6 respectively. The complete open reading frame of VP24 comprises 627 nucleotides and is depicted in SEQ ID NO. 11 together with the deduced amino acid sequence of VP19. The deduced amino acid sequence of VP24 has 208 residues and is separately depicted in SEQ ID NO. 12. The four proteins and their respective nucleotide sequences are specific for WSSV.

SUMMARY OF THE INVENTION

The present invention provides for the first time the means to produce recombinant vaccines to protect crustaceans against infection with WSSV. The four major proteins VP28, VP26, VP24 and VP19 of WSSV which have been identified and characterized were found to be suitable for use in the manufacture of a subunit vaccine to protect crustaceans against infections with WSSV. The cloning and characterization of the nucleotide sequences of the present invention provides for the production of these structural proteins of the WSSV using recombinant technology techniques. In this way, recombinant structural WSSV proteins can be obtained, which are substantially free from other WSSV proteins. The isolated structural WSSV proteins can be used to manufacture subunit vaccines to protect crustaceans against infection of WSSV. Alternatively, the nucleotide sequences encoding the structural proteins of the WSSV can be used to manufacture vector vaccines to protect crustaceans against the infection with WSSV. The nucleotide sequences of the present invention can furthermore be used for diagnostic purposes, for instance to detect the presence of WSSV in the field. Additionally, the WSSV proteins of the present invention can be used to produce WSSV specific antibodies. These antibodies can be used to produce WSSV vaccines for passive immunization of the crustaceans. The antibodies can also be used for diagnostic purposes such as the detection of WSSV in crustaceans or in the field.

BRIEF DESCRIPTION OF THE DRAWINGS

FIG. 5 Neutralization of WSSV in shrimp by antiserum raised against structural protein VP28. Negative control: shrimp receiving NaCl solution. Positive control: shrimp receiving WSSV but no antiserum. Pre-immune serum shrimp receiving WSSV and pre-immune serum. VP28 antiserum: shrimp receiving virus and anti-VP28 antiserum.

FIG. 6 Vaccination of shrimp with WSSV proteins. Negative control: shrimp receiving NaCl solution. Positive control: shrimp receiving NaCl and WSSV. Group 3: shrimp vaccinated with VP24. Group 4 shrimp vaccinated with VP26c. Group 5 shrimp vaccinated with VP28. Group 6: shrimp vaccinated with a mixture of VP24, VP26c and VP28.

DETAILED DESCRIPTION

Figure 1A:
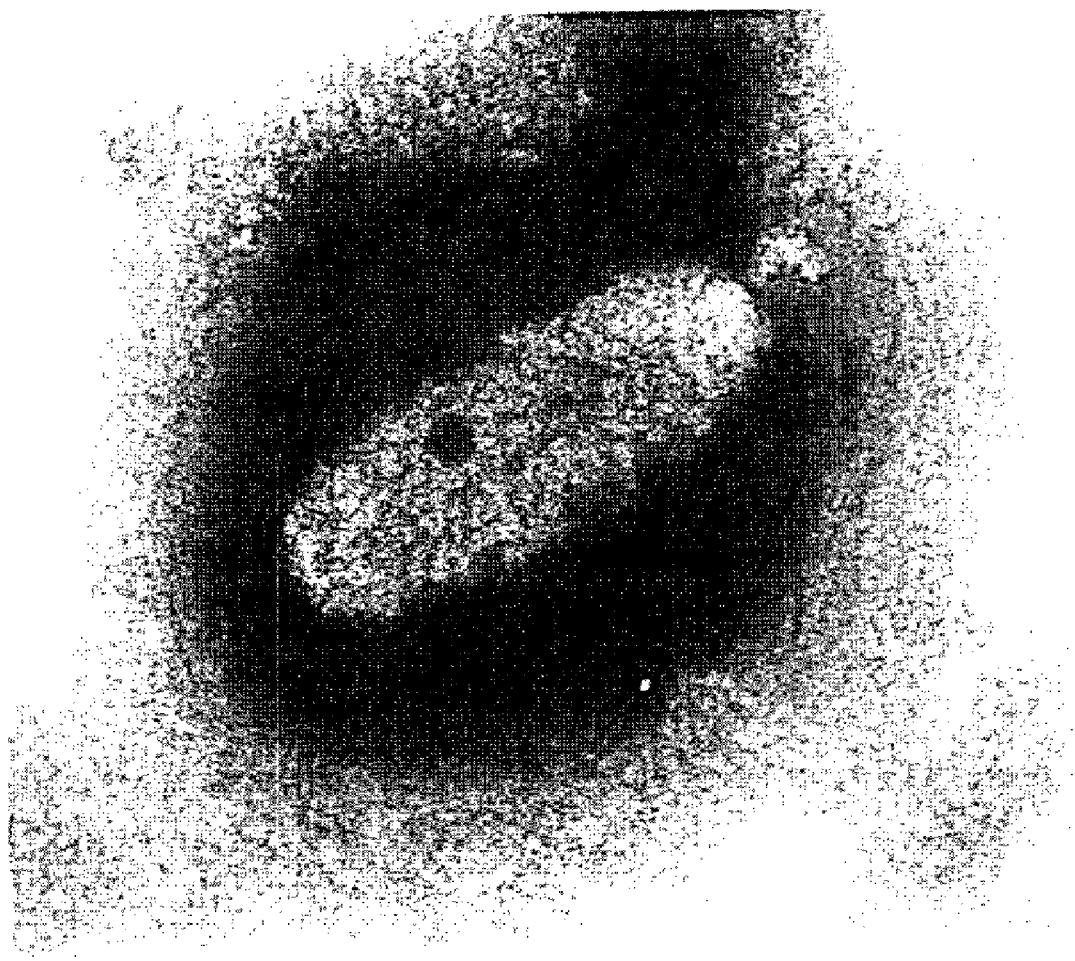
FIG. 1 WSSV proteins. (A) TEM picture of negatively stained intact virions. (B) TEM picture of negatively stained WSSV nucleocapsids. (C) 15% coomassie stained SDS PAGE gel of purified WSSV. Lane 1: Low molecular weight protein marker. Lane 2: purified "WSSV particles" from uninfected shrimp. Lane 3: purified WSSV particles. Lane 4: purified WSSV nucleocapsids.
Figure 1B:
Figure 1C:
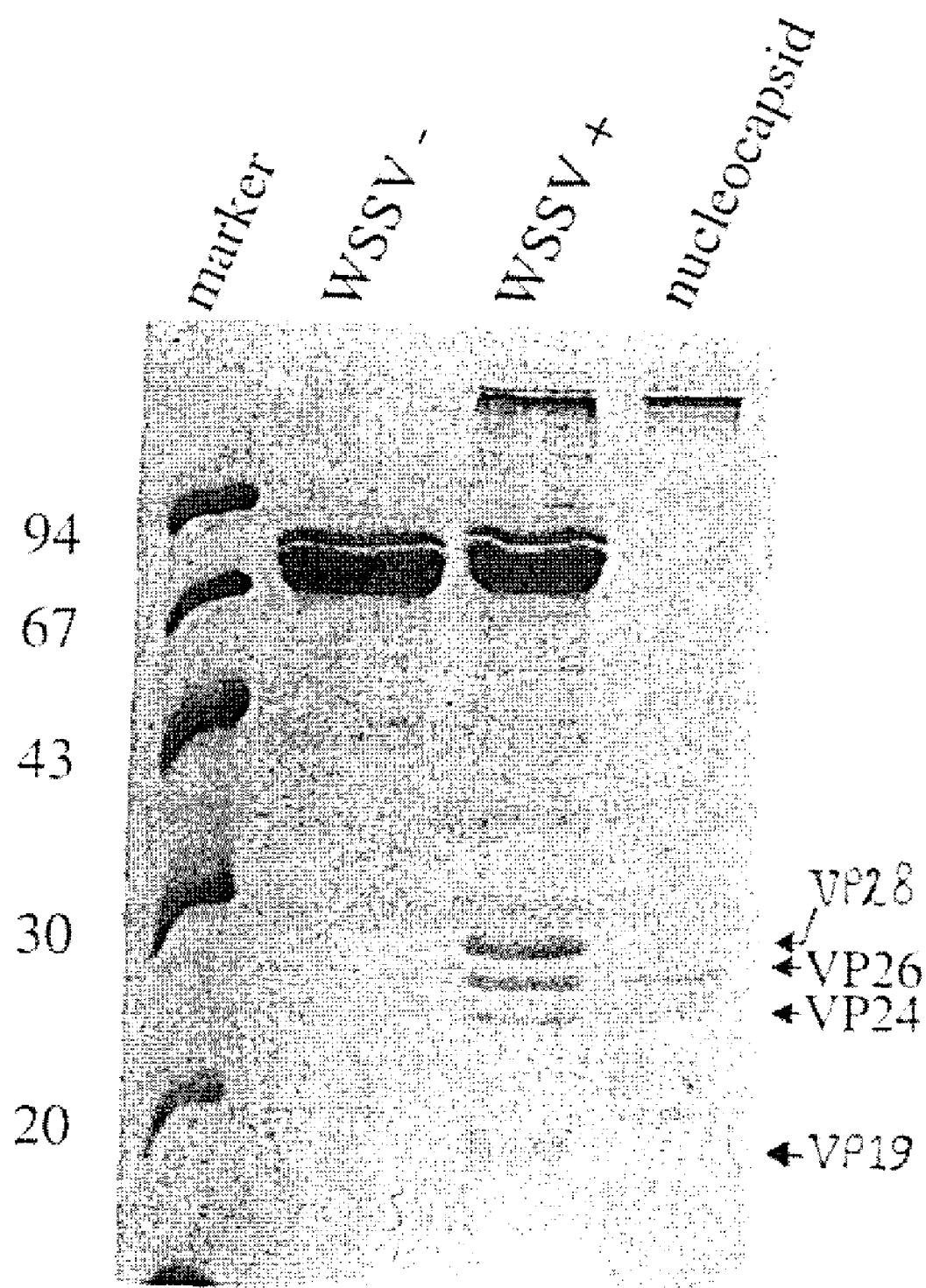

Thus in a first object the invention provides for the structural proteins of WSSV. More specifically the invention provides for structural proteins VP24, VP26, VP28 and VP19. In particular the invention provides for protein VP26 having an amino acid sequence depicted in FIG. 2b (SEQ ID NO. 3) or a derivative sequence thereof, such as, for example, SEQ ID NO. 10, and VP28 having an amino acid sequence depicted in FIG. 2c (SEQ ID NO. 4) or a derivative sequence thereof. The invention further provides for protein VP24 comprising the N-terminal amino acid sequence M H M W G V Y AA IL A G L T L I L V V I S I V V T N I E L N K K L D K K D K depicted in SEQ ID NO. 5 or a derivative thereof, and protein VP19 comprising the partial amino acid sequence I V L I S I (G/V) I L V L A V M N V (P/A/T) M G P K K D S depicted in SEQ ID NO. 6 or a derivative thereof. Preferably a protein VP24 has the amino acid sequence as depicted in SEQ ID NO. 12 or a derivative sequence thereof. It must be understood that proteins having a derivative sequence of the amino acid sequences depicted in SEQ ID NO 3, 4, 5, 6, 10 or 12 are also within the scope of the present invention. For the purpose of this invention, a derivative of the protein amino acid sequence is understood to be an amino acid sequence that comprises alterations compared to the amino acid sequence depicted in SEQ ID NO. 3, 4, 10 or 12 or the partial sequences depicted in SEQ ID NOS. 5 or 6, whereby said alterations do not affect the antigenic or immunogenic characteristics of the proteins.

For the purpose of this invention, antigenic characteristics of the proteins are understood to be the ability of the proteins to raise antibodies that are capable of recognizing and/or reacting with said WSSV proteins. Immunogenic characteristics are understood to be the ability of the proteins to induce a protective response in the crustaceans against WSSV infections.

The alterations that can occur in a sequence according to the present invention could, for instance, result from conservative amino acid substituations, deletions, insertions, inversions or additions of (an) amino acid (s) in the overall sequence Amino acid substitutions that are expected not to alter the immunological properties have been described. Amino acid replacements between related amino acids or replacements which have occurred frequently in evolution are, inter alia Ser/Ala, Ser/Gly, Asp/Gly, Asp/Asn, Ile/Val (see Dayhof, M.D., Atlas of protein sequence and structure, Nat. Biomed. Res. Found., Washington D.C., 1978 vol. 5, suppl. 3). Based on this information Lipman and Pearson developed a method for rapid and sensitive protein comparison (Science, 1985, vol. 227, 1435-1441) and determining the functional similarity between proteins and peptides having sequence homology. Several computer programs such as FASTA, TFASTA, BLAST and the like are available to determine sequence homology between a protein or peptide with given amino acid sequence and a derivative thereof; the optical match area between the sequences can be automatically determined by theses programs. Thus derivative proteins according to the invention are still capable to raise antibodies that recognize and can react with the structural WSSV proteins, or to induce a protective response in vaccinated crustaceans that protects them against WSSV infection. Other derivative proteins that can be used according to the invention are fragments of the WSSV proteins, provided said fragments are still capable to raise antibodies that recognize and can react with the structural WSSV proteins, or to induce a protective response in vaccinated crustaceans that protects them against WSSV infection.

In a second aspect the invention provides for a nucleic acid sequence encoding one or more structural proteins of WSSV. More preferably the present invention provides for a nucleic acid sequence encoding the major structural proteins VP24, VP26, VP28 and/or VP 19, respectively. In particular the present invention provides for a nucleic acid sequence of vp26, vp28 and vp24 depicted in SEQ ID NO. 1 or 9, SEQ ID NO. 2 or SEQ ID NO. 11 encoding VP26, VP28 and VP24 respectively. The respective nucleotide sequences start with the ATG codon encoding the first M residue of the deduced amino acid sequence up to the codon encoding the C-terminal amino acid residue. It must be understood that for the purpose of this invention nucleic acid sequences that have sequence homology with the sequences depicted in SEQ ID NO. 1 or SEQ ID NO. 2 or SEQ ID NO 9 or SEQ ID NO. 11 are also within the scope of the invention. The sequence homology for the purpose of this invention is considered to be at least 70%, preferably 75%, more preferably 80%, even more preferably 85%. Highly preferred are nucleic acid sequences that have sequence homology with the sequences depicted in SEQ ID NO. 1, 2, 9, or 11 of at least 90% more preferably 95%.

For the purpose of this invention sequence homology is determined by comparing the nucleotide sequence of interest with the corresponding part of the sequence depicted in SEQ ID NO. 1, SEQ ID NO. 2 or SEQ ID NO. 11. For the purpose of this invention the percentage sequence homology is defined as the percentage of identical nucleotides between the compared sequences. The sequence homology can be determined for instance by computer programs such as Blast N and the like. These programs automatically determine the optimal match area.

Nucleic acid sequences having sequence homology according to the invention can easily be isolated with one of the sequences depicted in SEQ ID NO 1, 2, 11 or 9 or with fragments of this sequence from closely related WSSV strains using routine cloning and hybridization techniques. For this purpose hybridization is carried out under stringent, preferably highly stringent conditions. Stringent hybridization conditions are understood to be washing conditions of 1×SSC, 0.1% SDS at a temperature of 65° C.; highly stringent conditions refer to washing conditions in which the concentration SSC is being lowered towards 0.3×SSC. The specific information should not be so narrowly interpreted so as to require exclusion of erroneously identified bases. The specific sequences disclosed herein can be readily used to isolate homologous nucleotide sequences from other strains.

A nucleic acid sequence that has sequence homology with one of the sequences depicted in SEQ ID No's 1, 2 or 11 encodes a protein having an amino acid sequence which comprises alterations compared to one of the amino acid sequences depicted in SEQ ID NO's 3, 4, 10 or 12 or one of the partial amino acid sequences depicted in SEQ ID No's 5 and 6, whereby said alterations do not affect the antigenic or immunogenic properties of said protein. An example of such homologous nucleotide sequence encoding a VP26 protein is the nucleotide sequence depicted in SEQ ID NO. 9, which encodes for a VP26 protein having alterations compared to the amino acid sequence depicted in SEQ ID NO 3.

The WSSV proteins according to the invention can be obtained via standard biochemical isolation and purification methods or they can be prepared via general recombinant technology. The nucleotide sequences according to the invention are particularly suitable to be used for the recombinant production of structural WSSV proteins, substantially free from other WSSV proteins. The nucleotide sequences are incorporated into a suitable expression vector capable of expressing the proteins, transforming a suitable host cell with said expression vector and culturing the host cell in a suitable medium. The expressed proteins can be isolated and purified from the cells or the medium. Suitable expression vectors are, amongst other, plasmids, cosmids, viruses and YAC's (Yeast Artifical Chromosomes) which comprise the necessary control regions for replication and expression. The expression vector can be brought to expression on a host cell. Suitable host cells are, for instance, bacteria, yeast cells, insect cells and mammalian cells. Such expression techniques are well known in the art (Sambrooke et al., Molecular Cloning: a Laboratory Manual, Cold Spring Harbor Laboratory Press, Cold Spring Harbor, 1989; King and Possee, 1992).

In a third aspect the invention provides for a vaccine comprising one or more of the structural viron proteins VP24, VP26, VP28 or VP19 of WSSV and a pharmaceutically acceptable carrier. More specifically, a vaccine according to the invention comprises virion protein VP24, VP26, VP28 or VP19 or a combination of two or more of said proteins. Preferably a vaccine according to the invention comprises VP24 comprising either the amino acid sequence depicted in SEQ ID NO 12 or the N-terminal amino acid sequence depicted in SEQ ID NO. 5 or a derivative sequence of either sequences, or VP26 comprising the amino acid sequence depicted in SEQ ID NO. 3, SEQ ID NO. 10, or a derivative sequence of either sequence, or VP28 comprising the amino acid sequence depicted in SEQ ID NO. 4 or a derivative sequence thereof, or VP19 comprising the N-terminal amino acid sequence depicted in SEQ ID NO. 6 or a derivative sequence thereof, or a combination of two or more of said proteins. More preferably a vaccine according to the invention comprises WSSV proteins VP26 and VP28, and optionally VP24.

In addition, the nucleic acid sequences according to the invention can be used to manufacture a vector vaccine to vaccinate crustaceans against WSSV infections. A vector vaccine is understood to be a vaccine in which a live, attenuated bacterium or virus has been modified so that they contain one or more heterologous nucleotide sequences inserted into their genetic material. These so called vector bacteria or viruses are capable of co-expressing the heterologous proteins encoded by the inserted nucleotides. Thus in a fourth aspect the invention provides for a vector vaccine comprising a live attenuated bacteria or virus and a pharmaceutically acceptable carrier, in which said bacteria or virus has been modified to comprise in its genetic material one or more of the nucleotide sequences of the present invention.

A vaccine according to the invention can be used to protect crustaceans such as shrimp, including but not limited to members from the Penaeidae family such as for example *P. monodon, P. vannamei, P. chinensis, P. merguensis,* or *Metapenaeus* spp.; prawns including but not limited to members from the Palaemonidae family such as for example *Macrobrachium* spp., or *Palaemon* spp.; lobsters including but not limited to members from the Palinuridae and Nephropidae family such as for example *Calinectes* spp., *Palinurus* spp., *Panuliris* spp. or *Homarus* spp.: crayfish including but not limited to members from the Astacidae family examples of which are *Astacus* spp., *Procambarus* spp., and *Oronectes* spp.; and crab including but not limited to members from the Cancridae and Portuidae family, examples of which are *Cancer* spp., *Callinectes* spp., *Carcinus* spp., and *Portunus* spp.

In addition, the nucleic acid sequences according to the invention can be used to manufacture a vector vaccine to vaccinate crustaceans against WSSV infections. A vector vaccine is understood to be a vaccine in which a live, attenuated bacterium or virus has been modified so that they contain one or more heterologous nucleotide sequences inserted into their genetic material. Thus in a fourth aspect the invention provides for a vector vaccine comprising a live attenuated bacteria or virus and a pharmaceutically acceptable carrier, in which said bacteria or virus has been modified to comprise in its genetic material one or more of the nucleotide sequences of the present invention.

A vaccine according to the invention can be prepared according to techniques well known to the skilled practitioner and described for instance in Remington's Pharmaceutical Sciences, $18^{th}$ edition (1990), eds. A. R. Gennaro et al., chapter 72, pp. 1389-1404, Philadelphia College of Pharmacy and Science.

Vaccines, sometimes referred to as a pharmaceutical formulation, according to the invention comprise an effective amount of one or more proteins, vector bacteria or virus according to the invention, and a pharmaceutically acceptable carrier. The term "effective" as used herein is defined as the amount sufficient to induce a protective response in the crustaceans. The amount of vector or protein will depend on the type of vector or protein, the route of administration, the time of administration, the species to be vaccinated as well as age, general health, temperature and diet.

In general, a dosage of 0.01 to 1000 μg protein per animal, preferably 0.5 to 500 μg, more preferably 0.1 to 100 μg protein per animal can be used. In case of viral vector vaccines in general a dosage of 103 to 108 pfu (plaque forming units) per animal can be used.

Pharmaceutically acceptable carriers that are suitable for use in a vaccine according to the invention are sterile and physiologically compatible such as for example sterile water, saline, aqueous buffers such as alkali metal phosphates (e.g. PBS), alcohols, polyols, and the like. In addition, a vaccine according to the invention may comprise other additives such as adjuvants, stabilizers, anti-oxidants, preservatives and etc.

Suitable adjuvants include but are not limited to aluminum salts or gels, carbomers, non-ionic blockcopolymers, tocopherols, monophosphorylllipid A, muramyldipeptide, oil emulsions, glucans, cytokines, saponins such as Quil A, and the like. The amount of adjuvant added depends on the nature of the adjuvant itself.

Suitable stabilizers for use in a vaccine according to the invention include but are not limited to carbohydrates such as sorbitol, mannitol, starch, sucrose, dextrin, and glucose, proteins such as albumin or casein, and buffers like alkaline phosphates.

Suitable preservatives include, amongst others thimerosal and merthiolate.

The vaccines according to the invention can be administered via injection, immersion, dipping, spray or aerosol, or per oral. Preferably the vaccine is administered to the crustaceans via immersion or per oral, especially in case of commercial aquaculture farms.

For oral administration the vaccine is preferably mixed with a suitable carrier for oral administration, e.g., cellulose, food or a metabolizable substance such as alpha-cellulose or different oils of vegetable or animal origin. Particularly preferred food carriers for oral delivery of the vaccine according to the invention are live-feed organisms which are able to encapsulate the vaccine. Suitable live-feed organisms include but are not limited to plankton-like non-selective filter feeders preferably members of Rotifera, *Artemia*, and the like. Highly preferred is the brine shrimp *Artemia* sp.

The proteins according to the invention can be used for the production of antibodies, using the general techniques available to the practitioner in the field. Preferably the proteins are used to produce specific monoclonal antibodies. Antibodies according to the invention can be prepared according to standard techniques. Procedures for immunizing animals, e.g. mice, with proteins and selection of hybridomas producing proteins specific monoclonal antibodies are well known in the art (see for example Cligan et al. (eds). Current protocols in Immunology 1992; Kohler and Milstein, Nature 256 pp. 495-497, 1975; Steenbakkers et al., Mol. Biol. Rep. 19, pp. 125-134, 1994). The obtained antibodies may be utilized in diagnostics to detect WSSV in the field or to detect the presence of WSSV in the crustaceans. The nucleotide sequences according to the invention are also suitable for use in diagnostics. Said sequences or fragments thereof can be used in for instance PCR technology to detect the presence of WSSV in the field, or in the crustaceans. Thus, in another aspect, the present invention provides for a diagnostic kit comprising one or more nucleotide sequences or antibodies according to the invention.

The antibodies raised against the proteins VP28, VP26, VP24 and CP19 according to the invention can further be used to manufacture antibody vaccines for the passive immunization of the crustaceans. Thus, in a further aspect, the present invention provides for a vaccine for passive immunization against WSSV said vaccine comprising antibodies raised against either VP28, VP26, VP24, or VP19 or a combination of two or more of said proteins. Such a vaccine can be prepared using standard techniques, as mentioned above. Preferably a vaccine for oral administration of the antibodies is prepared, in which the antibodies are mixed with an edible carrier such as fish food. More preferably, the vaccine is prepared from antibodies prepared in chicken eggs (IgY antibodies).

The following examples are to illustrate the invention and should not be interpreted to limit the invention in any way.

EXAMPLES

Methods

White Spot Syndrome Virus Production and Purification

The virus used in this study was isolated from infected *Penaeus monodon* shrimp from Thailand. Infected tissue was homogenized in TN buffer (20 mM Tris-HCl, 400 mM NaCl, pH 7.4). After centrifugation at 1,700×g for 10 min the supernatant was filtered (0.45 um filter). The filtrate was injected intramuscularly into healthy *P. monodon* in the lateral area of the fourth abdominal segment to initiate infection. After 4 days haemolymph was withdrawn from moribund shrimp and mixed with modified Alsever solution (Rodriquez et al., 1995) as an anticoagulant. After dilution in TNE (20 mM Tris-HCl, 400 mM NaCl, 5 mM EDTA, pH 7.4), the haemolymph was clarified from haemocytes at 1,700×g for 10 min at 4° C. The virus particles were sedimented by centrifugation at 45,000×g at 4° C. for 1 h and suspended from the pellet in TN.

The virus envelope was removed from the virus particles by treatment with Nonidet P40 (NP40). One percent NP40 was added to the virus solution and incubated for 30 min at room temperature with gentle rocking. The nucleocapsids were sedimanted at 80,000×g for 30 min at 4° C. The pellet was dissolved in TE (10 mM Tris-HCl, 1 mM EDTA, pH 7.5).

SDS-PAGE of Virion Suspensions

For protein analysis, the WSSV virion preparations (enveloped virions, the nucleocapsids and the negative control were analyzed in at 15% SDS-PAGE gel. Proteins were visualized in SDS-PAGE gel using coomassie brilliant blue staining.

Electron Microscopy

For transmission electron microscopy (TEM), virus suspension(s) were mounted on formvar-coated, carbon-stabilised nickel grids (400 mesh), negatively stained with phosphotungstic acid (2% PTA). The specimens were examined by use of a Philips CM12 electron microscope.

Nucleic Acid Purification

Viral DNA was isolated from purified virions by treatment with proteinase K (0.2 mg/ml) and sarcosyl (1%) at 45° C. for 3 h, followed by phenol/chloroform extraction and dialysis against TE (10 mM Tris-HCl, 1 mM EDTA, pH 7.5). The purity and concentration of the DNA was determined by agarose gel electrophoresis using a marker.

Plasmid Constructions

WSSV subgenomic fragments were cloned into pBluescript SK+ (Stratagene) and transformed into *E. coli* DH5α using standard techniques (Sambrook et al., 1989). DNA isolation, restriction enzyme digestion, agarose gel electrophoresis and colony lifting were carried out according to standard protocols. (Sambrook et alk., 1989). PCR was performed using custom designed and synthesized primers. DNA encoding the N-terminal of vp28 was amplified by PCR from total WSSV DNA using degenerated primers based on the N-terminal amino acid sequence of VP28. The forward primer used was 5' CAGAATTCTCDATNGTYTTNGTNAC 3' (SEQ ID NO. 7) and the reverse primer was 5' CAGAAT-TCATGGAYYTNWSNTTYAC 3' (SEQ ID NO. 8) with EcoRI sites (D=A, T or G; N=A, C, G or T; Y=C or T; W=A or T; S=C or G). The N-terminal of vp24 was amplified by PCR from total WSSV DNA using a set of degenerate PCR primers based on the N-terminal amino acid sequence of VP24. 5' CAGAATTCATGCAYATGTGGGGNGT 3' (SEQ ID NO. 13) was used as forward primer, and 5' CAGAAT-TCYTTRTCYTTYTTRTCIARYTT 3' (SEQ ID NO. 14) as reverse primer, both containing EcoRI sites.

DNA Sequencing and Computer Analysis

Plasmid DNA for sequencing was purified via the QIA prep Miniprep System or JETstar Plasmid Purification System (Qiagen, Inc.). Sequencing was performed using the universal pBluescript forward and reverse nucleotide primers and customer synthesized primers from both strands. Automatic sequencing was carried out using an Applied Biosystems automated DNA sequenced (Eurogentec, Belgium).

The generated sequences were analyzed with UWGCG computer programs (release 10.0). The DNA and the deduced amino acids sequences were compared with the updated GenBank/EMBL, SWISSPORT and PIR databases using the programs FASTA, TFASTA (Pearson & Lipman, 1988) and Blast (Altschul et al., 1997).

Cells and Viruses

*Spodoptera frugiperda* (Sf-AE-21) cells (Vaughn et al., 1977) were cultured in Grace's insect medium (GIBCO BRL) supplemented with 10% foetal calf serum (FCS). The E2-strain of *Autographa californica* nuclear polyhedrosis virus (AcMNPV) (Smith and Summers, 1982) was used as wild type (wt) virus. Routine cell culture maintenance and virus infection procedures were carried out according to published procedures (Summers and Smith, 1987; King and Possee, 1992).

Engineering of Recombinants

The Bac-to-Bac system (GIBCO BRL) was employed to verexpress WSSV VP24 (SEQ ID NO. 12), VP26 (SEQ ID NO. 3), VP26c (SEQ ID NO. 10) and VP28 (SEQ ID NO. 4) in insect cells. To facilitate detection and titration of Bac-to Bac recombinants upon infection of insect cells the Green Fluorescent Protein (GFP) gene was introduced into the pFastBac-DUAL vector downstream of the p10 promoter. The GFP gene was removed from plasmid pVL92GFP (Reilander et al., 1996) after digestion of this plasmid with XbaI and KpnI. The 700 by GFP-containing fragmen was isolated by agarose gel electrophoresis and GlassMAX purification (GIBCO BRL), blunt-ended using DNA polymearse and inserted into the SmaI site of multiple cloning region II of pFastBac-Dual downstream of the p10 promoter. The resulting plasmid was named pFastBac-D/GFP and contained region I for insertion of a foreign gene downstream of the polyhedrin promoter. Recombinant virus expressing only the GFP from the p10 promoter was constructed according to the Bac-to Bac system protocol (GIBCO BRL) and the virus was designated AcMNPV-GFP.

PCR was performed on the WSSV plasmids containing the putative complete open reading frames (ORFs) of vp26 (SEQ ID NO. 1) and vp28 (SEQ ID NO. 2) introducing a BamHi site at the 3' end of the ORFs and a HindIII site at the 5' end. Vp26 (SEQ ID NO 1) and vp28 (SEQ ID NO. 2) were first cloned into the pET28a vector (Novagen), excised with BamHI and NotI, and inserted downstream of the polyhedrin promoter of plasmid pFastBac-D/GFP. The resulting plasmids were named pFastBac-D/G-vp26 and p FastBac-D/G-vp28, respectively. Vp26c (SEQ ID NO. 9) and vp24 (SEQ ID NO. 11) were amplified by PCR on the plasmids containing the putative ORFs using primers introducing a BamHI site at the 5' end and EcoRI site on the 3' end. After digestion the ORFs of vp26c (SEQ ID NO. 9) and vp24 (SEQ ID NO. 11) were inserted downstream of the polyhedrin promoter of pFastBac-D/GFP, resulting in plasmids pFastBac-D/G-vp26c and pFastBac-D/G-vp24. Recombinant viruses expressing the GFP off the p10 promoter and VP24 (SEQ ID NO 12), VP26 (SEQ ID NO 3), VP26c (SEQ ID NO 10) or VP28 (SEQ ID NO 4) off the polyhedrin promoter were constructed according to the Bac-to-Bac system protocol (GIBCO BRL) and the viruses were designated AcMNPV-WSSVvp24, AcMNPV-WSSVvp26, AcMNPV-WSSVvp26c and AcMNPV-WSSVvp28, respectively.

SDS-PAGE, Protein Sequencing and Immunoblotting

Insect cells infected with wild type AcMNPV and recombinant AcMNPV expressing heterologous proteins (GFP, VP26, VP28) were analyzed in 15% SDS-PAG gels. Proteins were visualized using coomassie brilliant blue staining. Semi dry blotting was performed onto a polyvinylidene difluoride (PVDF) membrane (Bio-Rad) using a CAPS buffer (10 mM CAPS in 10% Methanol) or onto an Immobilon™-P (Millipore) using a Tris-Glycine buffer (25 mM Tris base, 192 mM glycine, 10% (v/v) methanol, pH 8.3). Proteins were visualized on the PVDF membrane using coomassie brilliant blue staining. Major protein bands from WSSV virion preparations were excised from the filter and N-terminally sequenced (ProSeq. Inc., Massachusetts).

Immobulon-P membranes were blocked in 2% low-fat milk powder (Campina, the Netherlands) in TBS (0.2 M NaCl, 50 mM Tris-HCl, pH 7.4). Immunodetection was performed by incubating the blot in a polyclonal rabbit anti-WSSV serum (a gift from Prof. P. C. Loh, University of Honolulu, Hi.) diluted 1:2000 in TBS with 0.2% low-fat milk powder for 1 h at room temperature. Subsequently, anti-rabbit antibody conjugated with horseradish peroxidase (Amersham) was used at a concentration of 1:2000 and detection was performed with an "Enhanced chemiluminescent-light detection kit" (Amersham).

VP28 Polyclonal Antibody

The major WSSV structural envelope protein VP28 was expressed in insect cells using baculovirus AcMNPV-WSSVvp28 and purified using a Prepcell (Biorad) and a fraction collector. Fractions containing VP28 were collected and concentrated. The purified VP28 protein was injected in a rabbit to produce a polyclonal antibody. The antibody was tested on western blots containing purified WSSV virions and reacted well with CP28 from the WSSV virions. The VP28 antiserum was used in a WSSV neutralization experiment.

WSSV Virus Stock

A White Spot Syndrome Virus (WSSV) virus stock was generated by purifying virus from haemolymph of crayfish *Procambarus clarkii*, which were injected intramuscularly with a low concentration WSSV one week earlier. The haemolymph was purified over a continuous sucrose gradient and a virus band was removed. After pelleting of the virus, the virus was dissolved in TE (pH 7.5). The virus stock was stored at −70° C. until use in the experiments.

Protein Vaccination

The major WSSV structural envelope protein VP28 (SEQ ID NO 4) and nucleocapsid proteins VP26c (SEQ ID NO. 10) and VP24 (SEQ ID NO. 12) were expressed in insect cells using baculovirus AcMNPV-WSSVvp28, AcMNPV-WSSVvp26c and AcMNPV-WSSVvp24, which express GFP off the p10 promoter and the WSSV structural proteins from the polyhedrin promoter. 3 days post infection the infected insect cells were harvested and disrupted by sonificatin. The supernatant was used to vaccinate *P. monodon*.

6 groups of shrimp were used in this experiment:

| Group # | Group Name | Vaccination | Booster | Challenge | # shrimp |
|---|---|---|---|---|---|
| 1 | Negative control | 330 mM NaCl | 330 mM NaCl | 330 mM NaCl | 10 |
| 2 | Positive control | 330 mM NaCl | 330 mM NaCl | WSSV | 10 |
| 3 | VP28 | VP28 | VP28 | WSSV | 15 |
| 4 | VP26c | VP26c | VP26c | WSSV | 15 |
| 5 | VP24 | VP24 | VP24 | WSSV | 15 |
| 6 | MIX | Mix | Mix | WSSV | 15 |

Figure 2A:
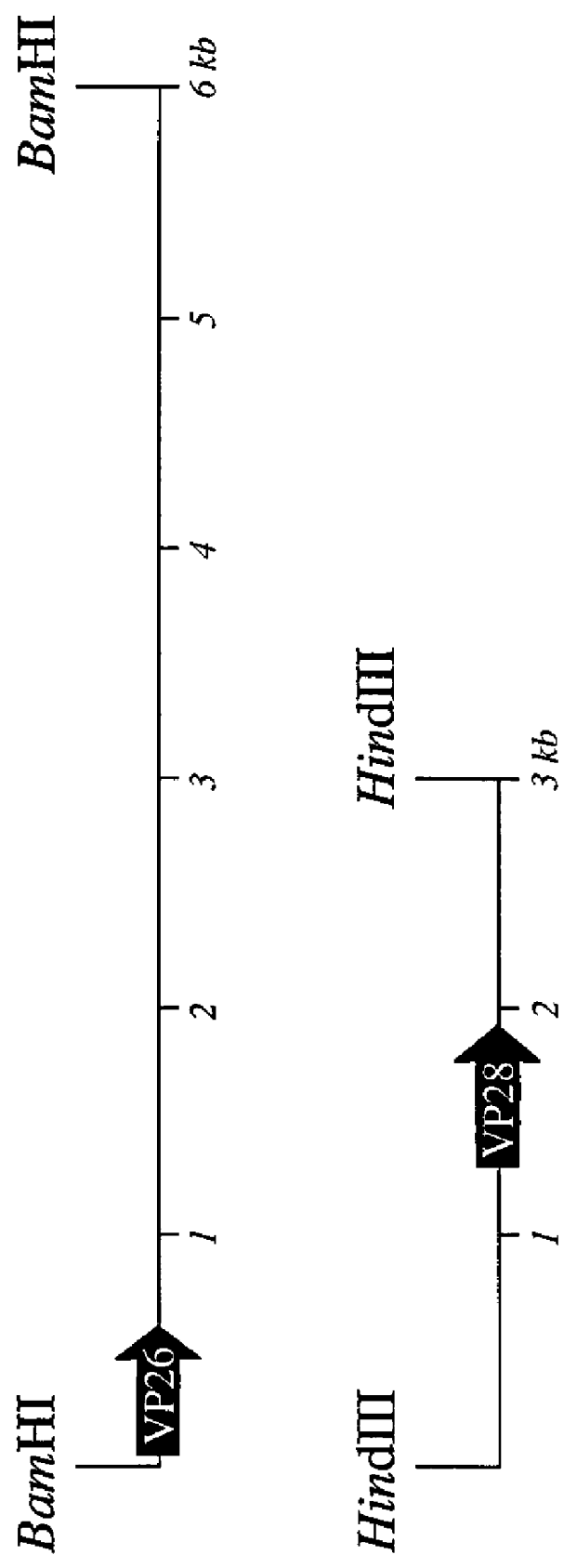
FIG. 2 Nucleotide sequence of WSSV VP26 and VP28. (A) Location of VP26 and VP28 and WSSV genomic fragments. (B) Nucleotide and protein sequence of VP26 (SEQ ID NO. 1 and SEQ ID NO. 3, respectively) and (C) of VP28 (SEQ ID NO. 2 and SEQ ID NO. 4, respectively. The ORF of vp26 and vp28, respectively, start at the ATG codon encoding the first M residue of the deduced amino acid sequence. The N-terminal sequences amino acids are bold faced; the location of putative N-glycosylation sites is underlined and of putative O-glycosylation sites double underlined. The nucleotide sequence of degenerated primer positions on VP28 are in italics.
Figure 3A:
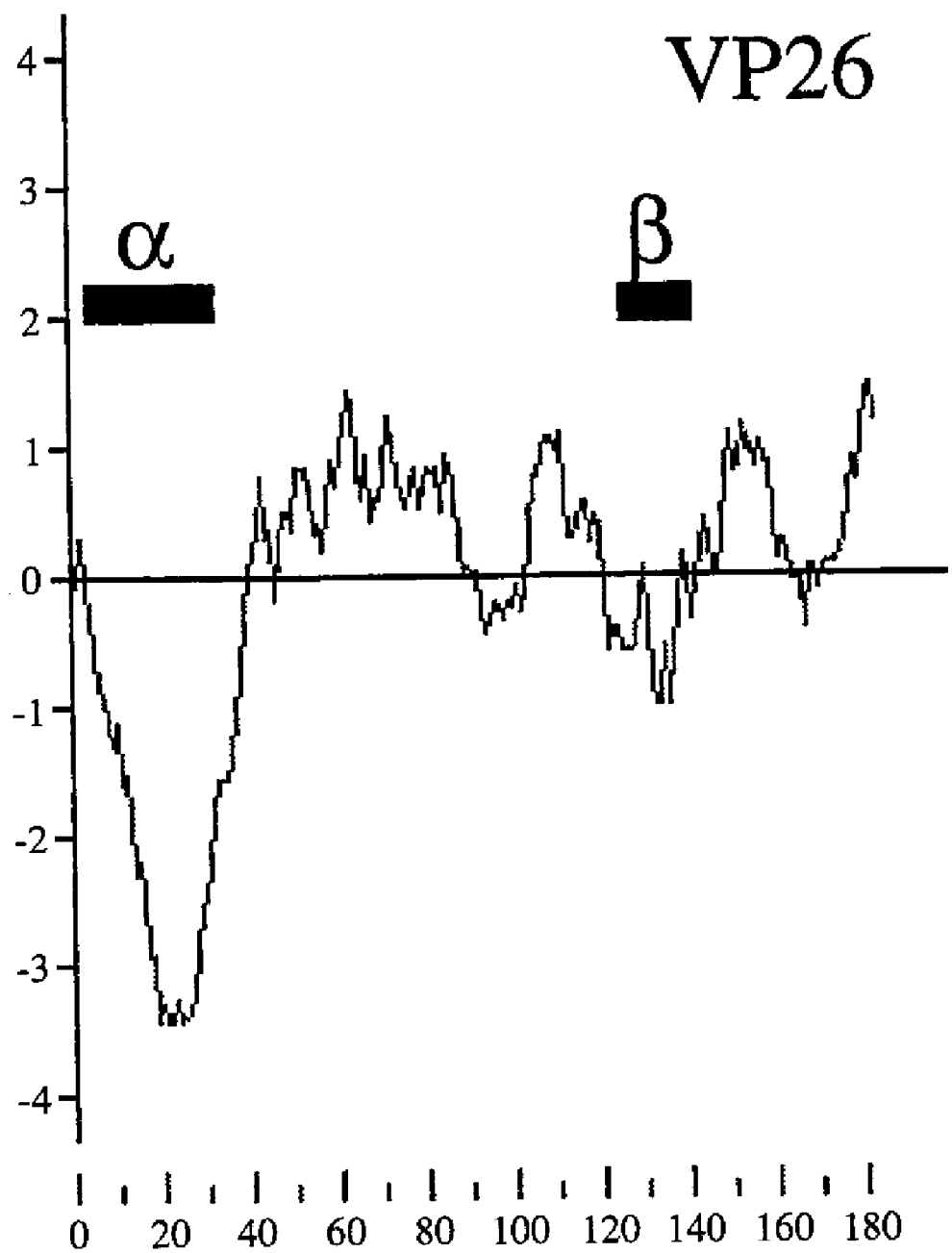
FIG. 3 Hydrophobicity plots of (A) VP26 and (B) VP28.

In the MIX equal volumes of the VP28, VP26c and VP24 solutions were mixed before injection. 5 days after vaccination, the shrimp obtain a booster injection. Two days later the challenge is performed by injection of WSSV (Stock virus, see neutralization experiment). After injection the shrimp were monitored for 6 days and dead shrimp were examined for the presence of WSSV by electron microscopy.

Results

Isolation of WSSV Proteins for Sequencing

*Penaeus monodon* shrimp were infected with WSSV by injection of a purified virus preparation intramuscularly. Four days after infection, virus was isolated from the haemolymph of the infected animals. As a negative control, haemolymph was taken from uninfected shrimp. These preparations were analyzed by electron microscopy for the presence and purity of WSSV virions. In the samples of uninfected animals, no virus particles were observed, but in samples of the infected animals, many mainly enveloped virions were observed (FIG. 1*a*). The viral envelope was removed from the virus particles after treatment with NP40 resulting in purified nucleocapsids (FIG. 1*b*), with a superficial segmented appearance characteristic for WSSV nucleocapsids (Durand et al., 1997). The proteins of the enveloped virons and the nucleocapsids were separated by SDS-PAGE (FIG. 1*c*.). Four major peptides were identified in virions with an apparent molecular mass of 28 (VP28), 26 (VP26), 24 (VP24), and 19 kDa (VP19), respectively. Several less prominent bands are also observed from which approximately six bands are located in the range of 30 to 65 kDa and at least seven weak protein bands ranging from 86 dDa to 130 kDa. Three major proteins bands, derived from the haemolymph are copurified with the virions and present in the range of 67 kDa to 78 kDa. Minor protein bands present in this area can not be observed in this gel (FIG. 1.) The sized found for the major WSSV proteins VP28 and VP19 are absent in the lane containing the purified nucleocapsids (FIG. 1*c*) and thus seem to be derived from the viral envelope or tegument. VP26 and VP24 were present in both the nucleocapsids and the virions, suggesting that they are derived from the nucloecapsid.

The content of the SDS-PAGE gel was transferred to a polyvinylidene diflouride membrane by semi dry blotting and the major viral protein bands were excised and sequenced. From VP28 and VP26 more than 40 amino acids were sequenced from the N-terminus (bold faced in FIGS. 2*b* and 2*c*, respectively). The VP26 N-terminal sequence contained M E F G N L T N L D V A I I A I L S I A I I A L I V I M V I M I V F N T R V G R S V V A N (SEQ ID NO. 3). N-terminal sequencing of VP28 gave the amino acid sequence M D L S F T L S V V S A I L A I T A V I A V F I V I F R Y H N T V T K T I E t H s D (SEQ ID NO. 4), of which the threonine at position 39 and the serine at position 41 are uncertain. Both N-terminal sequences are hydrophobic (FIG. 3). The N-terminal amino acid sequence obtained via N-terminal peptide sequencing for VP24 is M H M W G V Y A A I L A G L T L I L V V I S I V V T N I E L N K K L D K K D K (SEQ ID NO. 5). VP19 was found to be N-terminally blocked and a partial internal sequence of VP19 was obtained via CNBr digestion of N-terminal blocked peptide and gave the amino acid sequence I V L I S I (G/V) I L V L A V M N V (P/A/T) M G P K K D S (SEQ ID NO. 6). The amino acid residue at position 7 of the VP19 partial sequence could be a G or a V, and at position 17 a P, an A or T residue.

Localization and Sequence of the 24 kDa Protein Gene

Based on the N-terminal protein sequence of CP24 a set of degenerate PCR primers was developed, with 5' CAGAATTCATGCAYATGTGGGGNGT 3' (SEQ ID NO. 13) as forward primer, and 5' CAGAATTCYTTRTCYTTYTTRTCIARYTT 3' (SEQ ID NO. 14) as reverse primer, both containing EcoRI sites. PCR was performed using WSSV genomic DNA as template. A 133 bp-long fragment was obtained and, after purification from a 2% agarose gel, cloned into pBluescript SK+ and sequenced. The sequence of the PCR product corresponded with the N-terminal protein sequence (SEQ ID NO. 5) of WSSV VP24 and was used as prove in a coloby lift assay (Sambrook et alk., 1989) on WSSV plasmid libraries to identify the complete ORF for VP24. An 18 kbp BamHI fragment hybridizing with this fragment was selected for further analysis.

The complete vp24 ORF, encompassing 627 nucleotides, and the promoter region of this gene were found on the 18 kbp BamHI fragment. The translational start codon was in a favorable context (AAAATGC) for efficient eukaryotic translation initiation (Kozak, 1989). In the promoter region stretches of A/T rich sequence, but no consensus TATA box, were found. A polyA signal overlapped the translation stop codon. The vp24 ORF (SEQ ID NO 11) encoded a putative protein of 208 amino acids (SEQ ID NO 12) with an amino acid sequence containing the experimentally determined N-terminal sequence (SEQ ID NO 5) of VP24. VP24 has a theoretical size of 23 kDa and an isoelectric point of 8.7. Four potential sites for N-linked glycosylation (N-{P}-[ST]-{P}), one site for O-glycosylation (Hansen et al., 1998) and 9 possible phosphorylation sites ([ST]-X-X-[DE] or [ST-X-[RK]) were found within VP24, but it is not known whether any of these modifications do occur. No other motifs present in the PROSITE database were found in VP24. Computer analysis of the 208 amino acids showed that a strong hydrophobic region was present at the N-terminus of VP24, including a putative transmembrane $\alpha$ helix formed by amino acid 6 through 25. The algorithm of Garnier et al. (1978) predicted several other $\alpha$ helices and $\beta$-sheets along the protein.

Localization and Sequence of the 26 kDa Protein Gene

Partial WSSV genomic libraries of HindIII, and BamHI were constructed in pBluescript-SK+ (van Hulten et al., 2000) and terminal nucleotide sequences were obtained from many WSSV fragments. The nucleotide sequence coding for the N-terminal sequence of VP26 was present near a terminus of a 6 kb BamHI fragment (FIG. 2*a*). The sequence surrounding the methionine start codon (AAAATGG) was in conformity with the Kozak rule for efficient eukaryotic translation initiation (Kozak, 1989). Only 49 nucleotides (nt) of the untranslated leader of vp26 could be determined, extending to the terminal BamHI site (FIG. 2*a*)

The 6 kb BamHI fragment contained an open reading frame of 555 nt including those encoding the N-terminal amino acids of VP26 (FIG. 2*b*). A poly A signal is present 94 nucleotides (nt) downstream of the translational stop codon of vp26. This ORF (vp26) encoded a protein of 184 amino acids with a theoretical size of 20 kDa. The putative protein is basic with an isoelectric point of 9.4. Three potential sites for N-linked glycosylation (N-{P}-[ST]-{P}) are present and three putative O-glycosylation sites (FIG. 2b) were predicted using the program NetOglyc (Hansen et al., 1998). Thirteen possible phosphorylation sites ([ST]-X-X-[DE] or [ST-X-[RK]) were found, but no other motifs present in the PROSITE database. Hydrophobicity analysis of the 184 amino acid of VP26 showed that a strong hydrophobic region is present at the N-terminus of the protein (FIG. 3a). This region contained a putative transmembrane anchor formed by amino acid 12 through 34 in the form of a α-helix. The anchor was followed by a positively charged region containing two arginines, suggesting that the orientation of the C-terminal part is to the cytoplasmic side (Sonnhammer et al., 1998). Besides the transmembrane-spanning α helix, a potential β-sheet was found at position 127 through 141 using the algorithm of Garnier et al. (1978). Only one cysteine was present in the protein, indicating that no intraprotein disulfide cross-links can be formed. The cysteine was located in the C-terminal part of the protein, which was also the case in VP28.

Localization and Sequence of the 28 kDa Protein Gene

The amino acid sequence of CP28 was not available from translations of WSSV terminal fragment sequences. Based on the N-terminal sequence of this peptide a set of degenereated primers was developed. The forward primer was 5' CAGAAT-TCTCD ATNGTYTTNGTNAC 3' (SEQ ID NO. 7) and the reverse primer was 5' CAGAATTCATGGAYYTN WSNT-TYAC 3' (SEQ ID NO. 8) with EcoRI sites. The location of the primers on the sequence is indicated in FIG. 2c. PCR was performed using genomic WSSV DNA as template. A 128 bp-long fragment was obtained and, after purification from a 2.5% agarose gel, cloned into pBluescript SK+ and sequences. The nucleotide sequence encoded the N-terminal protein sequence of WSSV VP28 and this 128 by fragment was used in a colony life assay (Sambrook et al., 1989) on several WSSV plasmid libraries. A 3 km HindIII fragment hybridized with this fragment and was further analyzed.

The comlete ORF (vp28) of 612 nt and a promoter region of this gene was found on this 3 kb HindIII fragment (FIG. 2c). The methionine start codon (GTCATGG) is in a favorable context for efficient eukaryotic translation initiation (Kozak, 1989). In the promoter region no consensus TATA box was found but stretches of A/T rich regions were present. A polyA signal was observed 55 nucleotides downstream of the translation stop codon. The ORF coded for a putative protein of 204 amino acids, which included the N-terminal sequence amino acids. The theoretical size of this acidic protein was 22 kDa with an isoelectric point of 4.6. Five potential sites for N-linked glycosylation (N-{P}-[ST]-{P}), two sites for O-glycosylation (Hansen et al., 1998) (FIG. 2c) and 9 possible phosphorylation sites ([ST]-X-X-[DE] or [ST]-X-[RK]) were found. No other motifs present in the PROSITE database are found on VP28.

Figure 3B:
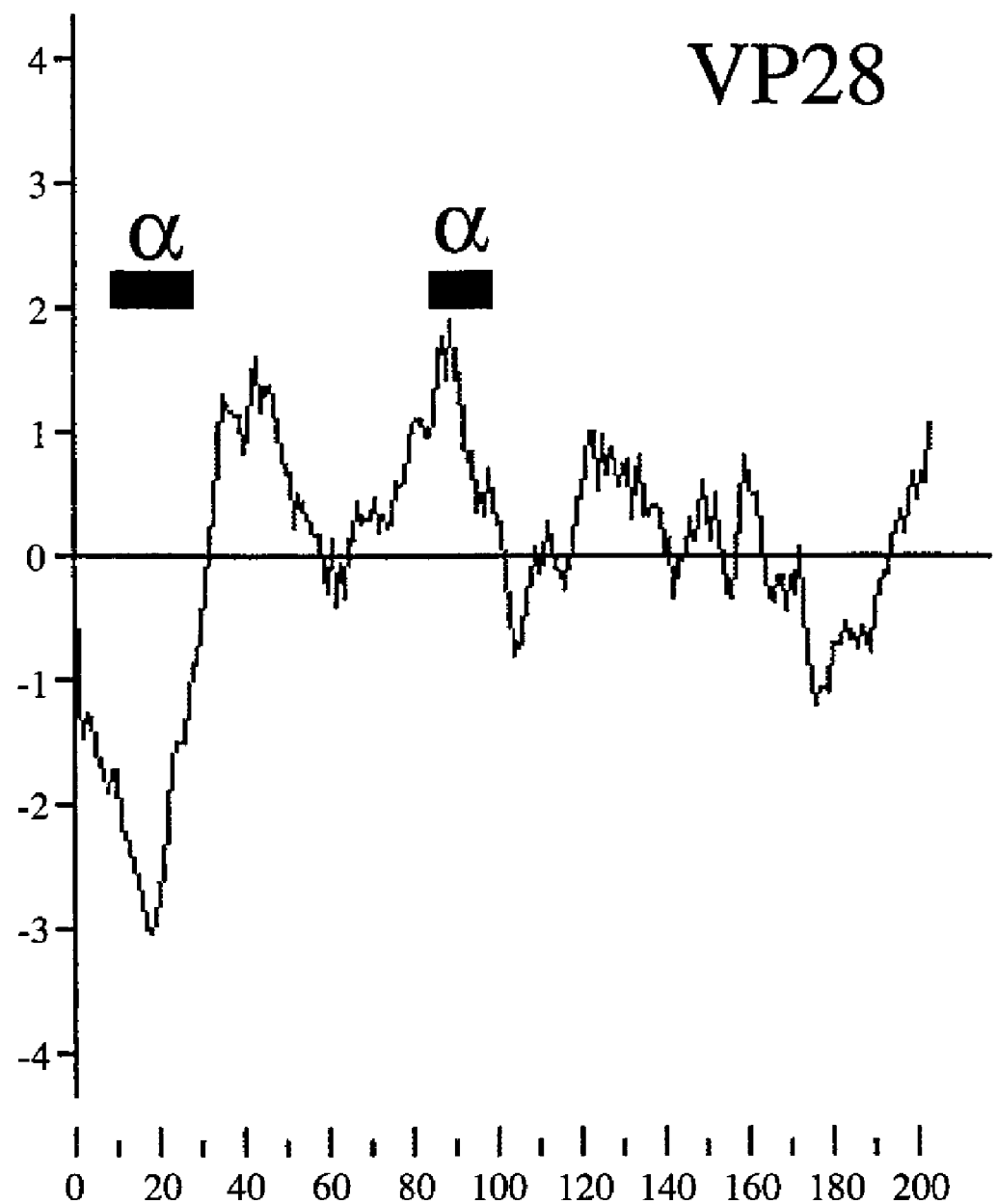

Computer analysis of the 204 amino acid proteins showed that a strong hydrophobic region was present at the N-terminus of the protein (FIG. 3b), including a putative transmembrane α-helix sequence formed by amino acid 9 through 27. As in VP26, this transmembrane anchor sequence is followed by a positively charged region suggesting that the protein may have an outside to inside orientation. At the C-terminal part of the sequence another hydrophobic region was found, which might constitute a transmembrane sequence. However, the algorithm of Garnier et al. (1978) did not predict an α helix at this position in VP28. The algorithm predicted a further α helix at position 89 to 99, but no β-sheets along the protein. As in VP26 only one cysteine was present in VP28. This cysteine was also located in the C-terminal part of the protein.

Expression and Analysis of Recombinant Vp24, Vp26 and Vp28.

The Bac-to-Bac system (GIBCO BRL) was used for the generation of recombinant baculoviruses expressing the putative WSSV virion proteins, VP24, VP26, VP26c and Vp28, in insect cells. The vp24, vp26, vp26c and vp28 genes (SEQ ID NO. 11, SEQ ID NO. 1, SEQ ID NO. 9 and SEQ ID NO. 2, respectively) were cloned downstream of the polyhedrin promoter from plasmid pFastBac-D/GFP, which contains a GFP gene downstream of the p10 promoter. The recombinant viruses generated from the pFastBac-D/GFP (control), and the plasmids with vp24, vp26, vp26c and vp28, were designated AcMNPV-GFP, AcMNPV-WSSVvp24, AcMNPV-WSSVvp26, AcMNPV-WSSVvp26c, and AcMNPV-WSS-Vvp28, respectively. All recombinant viruses expressed GFP off the p10 promoter; the latter four expressed in additional VP24, (SEQ ID NO. 12), VP26 (SEQ ID NO. 3), VP26c (SEQ ID NO. 10) and VP28 (SEQ Id NO. 4), respectively, off the polyhedrin promoter.

Figure 4A:
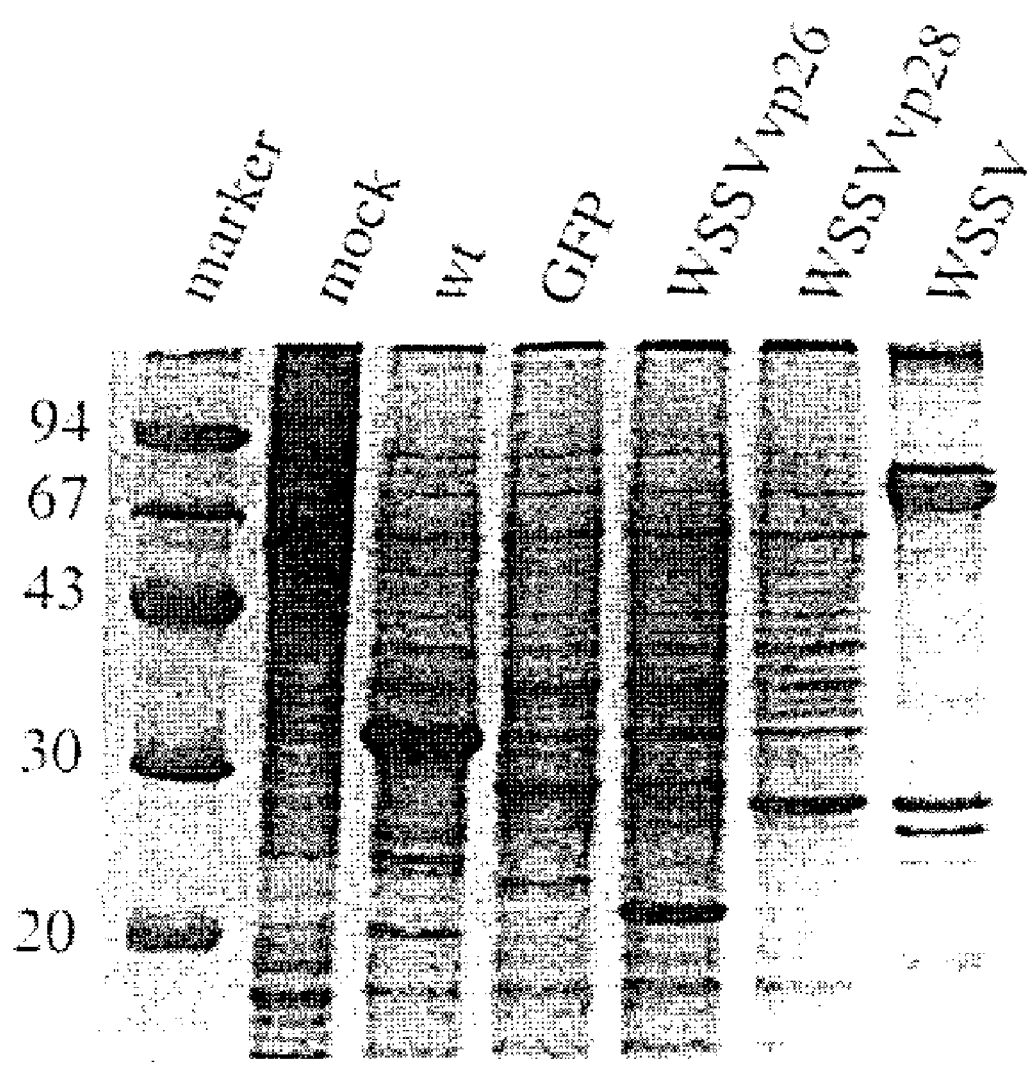
FIG. 4 Baculovirus expression of WSSV structural proteins in insect cells analyzed in a 15% SDS PAGE gel and western blot: (A) Coomassie stained gel with extracts of Sf21 cells. Lane 1: Low molecular weight protein marker. Lane 2: mock infection. Lane 3: AcMNPV-wt infection. Lane 4: AcMNPV-GFP infection. Lane 5: AcMNPV-WSSVvp26 infection. Lane 6: AcMNPV-WSSVvp28 infection. Lane 7: WSSV. (B) Western blot using a polyclonal antibody against purified WSSV.

Extracts of Sf21 infected with AcMNPV-wt, AcMNPV-GFP, AcMNPV-WSSVvp26, and AcMNPV-WSSVvp28 were analyzed in a 15% SDS-PAGE gel. In cells infected with wild type AcMNPV (FIG. 4a, lane 3) a 32 kDa band was visible which represents polyhedrin. In the lanes containing extracts of AcMNPV-GFP infected cells (lane 4) and cells infected with the recombinants expressing the WSS proteins (lanes 5 and 6), a GFP protein band was observed at approximately 29 kDa. The GFP expression in the cells infected with AcMNPV-GFP was stonger compared with GFP expression in the baculoviruses expressing WSSV proteins from the polyhedrin promoter (lanes 5 and 6). This was also readily observed after UV illumination of cells infected with the various AcMNPV recombinants, where the fluorescence of GFP in AcMNPV-GFP, infected cells is the strongest (not shown). The expression of the WSSV proteins from the polyhedrin promoter is significant higher compared to the expression of GFP from the p10 promoter (lane 5 and 6). A strong expression of a 21 kDa protein was observed in extracts of AcMNPV-WSSV vp26 infected cells, most likely representing WSS VP26 (lane 5). A strong expression of a 28 kDa protein was observed in the cells infected with AcMNPV-WSSVvp28 (lane 6). The position of FGP in these gels was confirmed by western analysis using anti-GFP antiserum (data not shown).

Figure 4B:
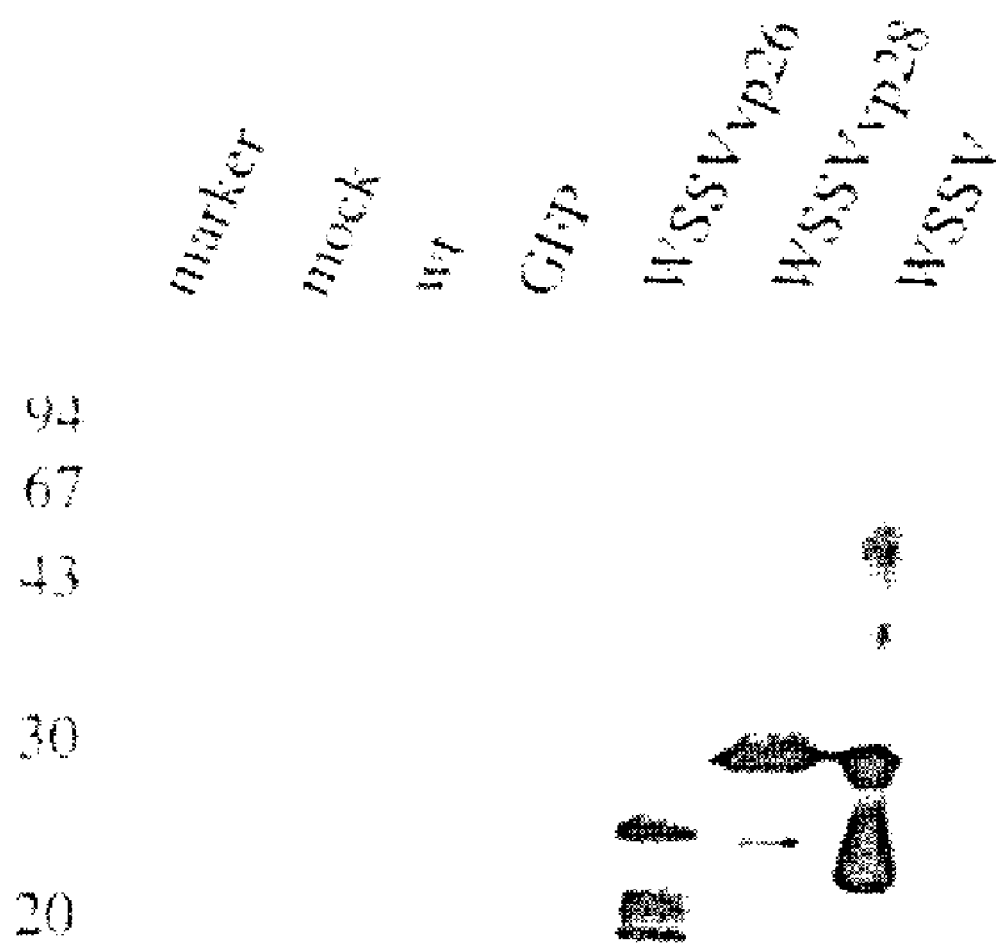

Western analysis was performed on samples of wild-type and recombinant AcMNPV infected sf21 cells electrophoreses in a SDS PAGE gel. A polyclonal antibody against WSSV virions was used to detect recombinant CP26 and VP28 (FIG. 4b). Both Vp26 and VP28 were well detected in these cell extracts. VP26 was detected at 21 kDa, in conformity with the Coomassie Brilliant Blue-stained gel (FIG. 4a, Lane 5; FIG. 4b, Lane 5). Recombinant Vp28 migrated at the same position as VP28 from WSSV virions, which is significant higher that the theoretical size of 22 kDa for this protein. The polyclonal antibody did not show major cross reactivity with insect cells (lane 2) or baculovirus (lanes 3 and 4) proteins, as observed from the very low background reaction in these samples.

Extracts of Sf21 cells infected with AcMnpV-WSSVvp26c and AcMNPV-WSSVvp24 were analyzed in a 15% SDS-PAGE gel. A low molecular weight marker and purified WSSV virions were also analyzed in the same gel. A weak band at 29 kDa was observed in the lanes containing the AcMNPV-WSSVvp26c and AcMNPV-WSSVvp24 infected cells, representing GFP, which was clearly observed after UV illumination of the infected cells. Furthermore in the lane with the AcMNPV-WSSVvp24, a clear band was observed at 24 kDa, corresponding with the position of the 24 kDa protein in the WSSV virions, a Western blot was made of this gel using a polyclonal antibody against WSSV virions. The 26 kDa band in AcMNPV-WSSVvp26c infected cells and the 24 kDa band in AcMNPV-WSSVvp24 infected cells were well detected.

Relatedness of Vp26 and Vp28

Homology searches with WSSV VP24, VP26, VP26c and VP28 were performed against GenBank/EMBL, SWISS-PORT and PIR databases using FASTA, TFASTA and BLAST. No significant homology could be found with the sequences in the GenBank, neither with baculovirus envelope or capsid proteins, nor with structural proteins from other large DNA viruses.

Neutralisation Experiment

The titer of the virus stock was obtained in a titration experiment. The virus stock was diluted $1\times10^7$ till $5\times10^{11}$ times and for each dilution 10 μl was injected intramuscularly into 10 shrimp (Penaeus monodon, 3-4 month old). The $1\times10^8$ dilution of the stock

| Group # | Group Name | Injection | # shrimp |
|---|---|---|---|
| 1 | Negative control | 330 mM NaCl | 10 |
| 2 | Positive control | WSSV | 10 |
| 3 | Pre-immune serum | WSSV + pre-immune serum | 15 |
| 4 | VP28 antiserum | WSSV + VP28 antiserum | 15 |

WSSV solution resulted in a mortality of 50% after 7-12 days and was used in further experiments.

4 groups of shrimp were used in the neutralization experiment:

The total amount of virus administered per shrimp is constant in all groups and equals 10 μl of the $1\times10^8$ dilution of the virus stock. The concentration of serum in group 3 and 4 is the same (perinjection: 1 μl WSSV and 9 μl of serum). After injection the shrimp were monitored for 4 weeks and dead shrimp were examined for the presence of WSSV by electron microscopy. The results are shown in FIG. 5.

None of the shrimp in group 1, the negative control, died of WSSV, therefore the mortality is 0%, In the positive control (group 2), 100% mortality was reached after 23 days. The group where pre-immune serum (that is serum taken before the rabbit was injected with VP28 proteins) was added to WSSV (group 3) reached 100% mortality in 25 days. When VP28 antiserum was added to WSSV (group 4), all shrimp survived resulting in 0% mortality. These results show that VP28 antiserum can neutralize WSSV infection in P. Monodon.

Protein Vaccination

Groups 3-6 were injected with 5 μl (vaccination) and 10 ul (booster) of the different protein solutions. For the vaccination group 3 received 2.5 μg VP28 protein, group 4 received 3.6 μg VP26c protein and group 5 received 0.7 μg of VP24 protein. Group 6 received a mix consisting of equal volumes of VP28, VP26c, and VP24 solution, resulting in a total amount of 2.7 μg protein. For the booster the shrimp received higher amounts of protein: 9.6 μg of VP28 protein for group 3, 5.7 μg of VP26c protein for group 4, 5.9 μg of VP24 protein for group 5 and a total amount of 7.1 μg protein for group 6. All groups of shrimp were injected with 10 μl of a $1\times10^8$ dilution of the stock WSSV solution.

The results of the vaccination are presented in FIG. 6. None of the shrimp in group 1, the negative control, died of WSSV, therefore the mortality is 0%. In group 2, shrimp start dying of WSSV infection after 1 day and mortality is increasing. Although these shrimp received the same dosage of WSSV virus as the shrimp in the neutralization experiment, the shrimp in group 2 are dying earlier. This is probably the result of stress caused by the multiple injections that the shrimp received in this experiment. In group 3-5 (shrimp vaccinated with VP24, VP26c and VP28, respectively) mortality was delayed, while in group 6 (shrimp vaccinated with an mixture of VP24, VP26c and VP28), none of the shrimp dies of WSSV, hence the mortality is 0%. Optimizing the dosage of the individual proteins in vaccination will also result in an increased protective effect against WSSV infection.

REFERENCES

Altschul, S., Madden, T., Schaffer, A., Zhang, J., Zhang, Z., Miller, W., and Lipman, D. (1997). Gapped BLAST and PSI-BLAST: a new generation of protein database search programs. Nucleic Acids Res. 25, 3389-3402.

Durand, S., Lightner, D. V., Redman, R. M., and Donami, J. R. (1997) Ultrastructure and morphogenesis of White Spot Syndrome Baculovirus (WSSV). Diseases Aquat. Organisms 29, 205-211

Flegel, T. W. (1997). Major viral diseases of the black tiger prawn (Penaeus monodon) in Thailand. World J. Microbiol. Biotechnol. 13, 433-442

Francki, R. I. B., Fauquest, C. M., Knudson, D. L., and Brown, F. (1991). "Classification and Nomenclature of Viruses: Fifth Report of the International Committee on Taxonomy of Viruses". Springer-Verlag, New York.

Garnier, J., Osguthorpe, D. J. and Robson, B. (1978) Analysis of the accuracy and implication of simple method for predicting the secondary structure of globular proteins. J. Mol. Biol. 120, 97-120

Hansen, J. E., Lunc, O., Tolstrup, N., Gooley, A. A., Williams, K. L., and Brunak, S. (1998). NetOglyc: Prediction of mucin type O-glycosylation sites based on sequence context and surface accessibility, Glycoconj. J. 15, 115-130.

King, L. A., and Possee, R. D. (1992). "The baculovirus expression system." Chapman & Hall, London.

Kozak, M. (1989). The scanning model for translation: an update. J. Cell Biol. 108, 229-241.

Lo, C. F., Hsu, H. C., Tsai, M. F., Ho, C. H., Peng, S. E., Kou, G. H., and Lightner, D. V. (1999). Specific genomic fragment analysis of different geographical clinical samples of shrimp white spot syndrome virus. Diseases Aquat. Organisms.

Murphy, F. A., Fauquest, C. M., Bishiop, D. H. L., Chabrail, S. A., Jarvis, A. W., Martelli, F. P., Mayo, M. A., and Summers, M. D. (1995). "Classification and Nomenclature of Viruses: Sisth Report of the Inernation Committee on Taxonomy of Viruses.". Virus Taxonomy Springer-Verlag, New York.

Pearson, W. R., and Lipman, D. J. (1988). Improved tools for biological sequence analysis. Proc. Natl. Acad. Sci. USA 85, 2444-2448.

Reilander, H., Haase, W., and Maul, G. (1996). Functional expression of the Aequorea victoria green fluorescent protein in insect cells using the baculovirus expression system. Biochem. Biophys. Res. Commun. 219, 14-20.

Rodriquex, J., Boulo, V., Mialhe, E., and Bachere, E. (1995). Characterisation of shrimp haemocytes and plasma components by monoclonal antibodies. J. Cell Sci. 108, 1043-1050.

Sambrook, J., Fritsch, E. F., and Maniatis, T. (1989). "Molecular Cloning: A laboratory Manual." 2 ed. Cold Spring Harbor Laboratory, New York Smith, G. E., and Summers, M. D. (1978). Analysis of baculovirus genomes with restrictin endonucleases. *Virology* 89, 517-527

Sonnhammer, E. L. L., von Heijne, G. and Krogh, A. (1998) A hidden Markov model for predicting transmembrane helices in protein sequences. In Proc. Sixth Int. Conf. On Intelligent Systems for Molecular Biology (J. Glasgow et al., Eds), p. 175-185, AAAI Press.

Van Hulten, M. C. W., Tsai, M. F., Schipper, C. A., Lo, C. F., Kou, G. H., and Vlak, J. M. (2000). Analysis of a genomic segment of White Spot Syndrome Virus of shrimp containing ribonucleotide reductase genes and repeat regions. *Journal of General Virology*, 81, 307-316.

Van Hulten, M. C. W., Westenberg, M., Goodall, S. D. & Vlak, J. M. (2000). Identification of two major viron protein genes of white spot syndrome virus of shrimp. *Virology* 266, 227-236.

Vaughn, J. L., Goodwin, R. H., Tompkins, G. J., and McCawley, P. W. (1977). The establishment of two cell lines from the insect *Spodoptera frugiperda* (*Lepidoptera*; Noctuidae). In Vitro 13, 213-7.

Wonteerasupaya, C., Vickers, J. E., Sriurairatana, S., Nash, G. L., Akarajamorn, A., Boonsaeng, V., Panyim, S., Tassanakajon, A., Withyachumarnkul, B., and Flegel, T. W. (1995) A non-occluded, systemic baculovirus that occurs in cells of ectodermal and mesodermal origin and causes high mortality in the black tiger prawn *Penaeus monodon*. *Diseases Aquat. Organisms* 21, 69-77

Yang, F., Wang, W., Chen, R. Z., and Xu, X. (1997). A simple and efficient method for purification of prawn baculovirus DNA. *J. Virol. Meth.* 67, 1-4

---

We claim:

1. An isolated and purified white spot syndrome envelope protein having the amino acid sequence depicted in SEQ ID NO. 4.

2. A pharmaceutical composition for treatment of white spot syndrome in crustaceans comprising an immunogenically effective amount of an envelope protein set forth as SEQ ID NO. 4 and a pharmaceutically acceptable carrier.

3. A method for immunizing crustaceans against White Spot Syndrome, wherein the method comprises administering an effective amount of a pharmaceutical composition comprising a pharmaceutically acceptable carrier and an envelope protein comprising the amino acid sequence depicted in SEQ ID NO. 4.

4. The method according to claim 3, wherein the pharmaceutical composition further comprises at least one additional white spot syndrome virus protein.

* * * * *

SEQUENCE LISTING

<160> NUMBER OF SEQ ID NOS: 14

<210> SEQ ID NO 1
<211> LENGTH: 555
<212> TYPE: DNA
<213> ORGANISM: white spot syndrome baculovirus

<400> SEQUENCE: 1

```
atggaatttg gcaacctaac aaacctggac gttgcaatta ttgcaatctt gtccattgca      60
atcattgctc taatcgttat catggttata atgattgtat tcaacacacg tgttggaaga     120
agcgtcgtcg ctaattatga tcagatgatg cgagtcccaa ttcaaagaag ggcaaaggta     180
atgtcaattc gtggagagag gtcctacaat actcctcttg gaaaggtggc catgaagaat     240
ggtctctccg ataaggacat gaaggatgtt tctgctgatc ttgtcatctc taccgtcaca     300
gccccaagga ctgatcccgc tggcactggg gccgagaact ctaacatgac tttgaagatc     360
ctcaacaaca ctggcgtcga tctcttgatc aacgacatta ctgttcggcc aactgttatt     420
gcaggaaaca ttaagggaaa tactatgtcg aacacttact tctcgagcaa ggacattaaa     480
tcttcatctt caaaaattac cctcattgac gtgtgcagca aatttgaaga cgcgcagcct     540
tcgaagctac aatga                                                       555
```

<210> SEQ ID NO 2
<211> LENGTH: 615
<212> TYPE: DNA
<213> ORGANISM: white spot syndrome baculovirus

<400> SEQUENCE: 2

```
atggatcttt ctttcactct ttcggtcgtg tcggccatcc tcgccatcac tgctgtgatt      60
gctgtattta ttgtgatttt taggtatcac aacactgtga ccaagaccat cgaaacccac     120
acagacaata tcgagacaaa catggatgaa aacctccgca ttcctgtgac tgctgaggtt     180
ggatcaggct acttcaagat gactgatgtg tcctttgaca gcgacacctt gggcaaaatc     240
aagatccgca atggaaagtc tgatgcacag atgaaggaag aagatgcgga tcttgtcatc     300
actcccgtgg agggccgagc actcgaagtg actgtgggc agaatctcac ctttgaggga     360
acattcaagg tgtggaacaa cacatcaaga aagatcaaca tcactggtat gcagatggtg     420
```

```
ccaaagatta acccatcaaa ggcctttgtc ggtagctcca acacctcctc cttcaccccc    480
gtctctattg atgaggatga agttggcacc tttgtgtgtg gtaccacctt tggcgcacca    540
attgcagcta ccgccggtgg aaatctttc gacatgtacg tgcacgtcac ctactctggc    600
actgagaccg agtaa                                                     615
```

```
<210> SEQ ID NO 3
<211> LENGTH: 184
<212> TYPE: PRT
<213> ORGANISM: white spot syndrome baculovirus

<400> SEQUENCE: 3
```

Met Glu Phe Gly Asn Leu Thr Asn Leu Asp Val Ala Ile Ile Ala Ile
1               5                   10                  15

Leu Ser Ile Ala Ile Ile Ala Leu Ile Val Ile Met Val Ile Met Ile
                20                  25                  30

Val Phe Asn Thr Arg Val Gly Arg Ser Val Val Ala Asn Tyr Asp Gln
            35                  40                  45

Met Met Arg Val Pro Ile Gln Arg Arg Ala Lys Val Met Ser Ile Arg
        50                  55                  60

Gly Glu Arg Ser Tyr Asn Thr Pro Leu Gly Lys Val Ala Met Lys Asn
65                  70                  75                  80

Gly Leu Ser Asp Lys Asp Met Lys Asp Val Ser Ala Asp Leu Val Ile
                85                  90                  95

Ser Thr Val Thr Ala Pro Arg Thr Asp Pro Ala Gly Thr Gly Ala Glu
            100                 105                 110

Asn Ser Asn Met Thr Leu Lys Ile Leu Asn Asn Thr Gly Val Asp Leu
        115                 120                 125

Leu Ile Asn Asp Ile Thr Val Arg Pro Thr Val Ile Ala Gly Asn Ile
130                 135                 140

Lys Gly Asn Thr Met Ser Asn Thr Tyr Phe Ser Ser Lys Asp Ile Lys
145                 150                 155                 160

Ser Ser Ser Ser Lys Ile Thr Leu Ile Asp Val Cys Ser Lys Phe Glu
                165                 170                 175

Asp Ala Gln Pro Ser Lys Leu Gln
            180

```
<210> SEQ ID NO 4
<211> LENGTH: 204
<212> TYPE: PRT
<213> ORGANISM: white spot syndrome baculovirus

<400> SEQUENCE: 4
```

Met Asp Leu Ser Phe Thr Leu Ser Val Val Ser Ala Ile Leu Ala Ile
1               5                   10                  15

Thr Ala Val Ile Ala Val Phe Ile Val Ile Phe Arg Tyr His Asn Thr
                20                  25                  30

Val Thr Lys Thr Ile Glu Thr His Thr Asp Asn Ile Glu Thr Asn Met
            35                  40                  45

Asp Glu Asn Leu Arg Ile Pro Val Thr Ala Glu Val Gly Ser Gly Tyr
        50                  55                  60

Phe Lys Met Thr Asp Val Ser Phe Asp Ser Asp Thr Leu Gly Lys Ile
65                  70                  75                  80

Lys Ile Arg Asn Gly Lys Ser Asp Ala Gln Met Lys Glu Glu Asp Ala
                85                  90                  95

```
Asp Leu Val Ile Thr Pro Val Glu Gly Arg Ala Leu Glu Val Thr Val
            100                 105                 110

Gly Gln Asn Leu Thr Phe Glu Gly Thr Phe Lys Val Trp Asn Asn Thr
        115                 120                 125

Ser Arg Lys Ile Asn Ile Thr Gly Met Gln Met Val Pro Lys Ile Asn
    130                 135                 140

Pro Ser Lys Ala Phe Val Gly Ser Ser Asn Thr Ser Ser Phe Thr Pro
145                 150                 155                 160

Val Ser Ile Asp Glu Asp Glu Val Gly Thr Phe Val Cys Gly Thr Thr
                165                 170                 175

Phe Gly Ala Pro Ile Ala Ala Thr Ala Gly Gly Asn Leu Phe Asp Met
            180                 185                 190

Tyr Val His Val Thr Tyr Ser Gly Thr Glu Thr Glu
        195                 200

<210> SEQ ID NO 5
<211> LENGTH: 39
<212> TYPE: PRT
<213> ORGANISM: white spot syndrome baculovirus

<400> SEQUENCE: 5

Met His Met Trp Gly Val Tyr Ala Ala Ile Leu Ala Gly Leu Thr Leu
1               5                   10                  15

Ile Leu Val Val Ile Ser Ile Val Val Thr Asn Ile Glu Leu Asn Lys
            20                  25                  30

Lys Leu Asp Lys Lys Asp Lys
        35

<210> SEQ ID NO 6
<211> LENGTH: 24
<212> TYPE: PRT
<213> ORGANISM: white spot syndrome baculovirus
<220> FEATURE:
<221> NAME/KEY: misc_feature
<222> LOCATION: (7)..(7)
<223> OTHER INFORMATION: Xaa can be any naturally occurring amino acid
<220> FEATURE:
<221> NAME/KEY: misc_feature
<222> LOCATION: (17)..(17)
<223> OTHER INFORMATION: Xaa can be any naturally occurring amino acid

<400> SEQUENCE: 6

Ile Val Leu Ile Ser Ile Xaa Ile Leu Val Leu Ala Val Met Asn Val
1               5                   10                  15

Xaa Met Gly Pro Lys Lys Asp Ser
            20

<210> SEQ ID NO 7
<211> LENGTH: 25
<212> TYPE: DNA
<213> ORGANISM: Artificial
<220> FEATURE:
<223> OTHER INFORMATION: Probe or primer
<220> FEATURE:
<221> NAME/KEY: misc_feature
<222> LOCATION: (14)..(14)
<223> OTHER INFORMATION: n is a, c, g, or t
<220> FEATURE:
<221> NAME/KEY: misc_feature
<222> LOCATION: (20)..(20)
<223> OTHER INFORMATION: n is a, c, g, or t
<220> FEATURE:
<221> NAME/KEY: misc_feature
<222> LOCATION: (23)..(23)
<223> OTHER INFORMATION: n is a, c, g, or t
```

<400> SEQUENCE: 7
cagaattctc datngtyttn gtnac                                    25

<210> SEQ ID NO 8
<211> LENGTH: 25
<212> TYPE: DNA
<213> ORGANISM: Artificial
<220> FEATURE:
<223> OTHER INFORMATION: Probe or primer
<220> FEATURE:
<221> NAME/KEY: misc_feature
<222> LOCATION: (17)..(17)
<223> OTHER INFORMATION: n is a, c, g, or t
<220> FEATURE:
<221> NAME/KEY: misc_feature
<222> LOCATION: (20)..(20)
<223> OTHER INFORMATION: n is a, c, g, or t

<400> SEQUENCE: 8
cagaattcat ggayytnwsn ttyac                                    25

<210> SEQ ID NO 9
<211> LENGTH: 615
<212> TYPE: DNA
<213> ORGANISM: white spot syndrome baculovirus

<400> SEQUENCE: 9
atggaatttg gcaacctaac aaacctggac gttgcaatta ttgcaatctt gtccattgca    60
atcattgctc taatcgttat catggttata atgattgtat caacacacg tgttggaaga   120 agcgtcgtcg ctaattatga tcagatgatg cgagtcccaa ttcaaagaag ggcaaaggta   180
atgtcaattc gtggagagag gtcctacaat actcctcttg gaaaggtggc catgaagaat   240
ggtctctccg ataaggacat gaaggatgtt tctgctgatc ttgtcatctc taccgtcaca   300
gccccaagga ctgatcccgc tggcactggg gccgagaact ctaacatgac tttgaagatc   360
ctcaacaaca ctggcgtcga tctcttgatc aacgacatta ctgttcggcc aactgttatt   420
gcaggaaaca ttaagggaaa tactatgtcg aacacttact tctcgagcaa ggacattaaa   480
tcttcatctt caaaaattac cctcattgac gtgtgcagca aatttgaaga cggcgcagcc   540
ttcgaagcta caatgaacat tggattcacc tccaagaatg tgatcgatat caaggacgaa   600
atcaagaaga agtaa                                                   615

<210> SEQ ID NO 10
<211> LENGTH: 204
<212> TYPE: PRT
<213> ORGANISM: white spot syndrome baculovirus

<400> SEQUENCE: 10

Met Glu Phe Gly Asn Leu Thr Asn Leu Asp Val Ala Ile Ile Ala Ile
1 5 10 15

Leu Ser Ile Ala Ile Ile Ala Leu Ile Val Ile Met Val Ile Met Ile
20 25 30

Val Phe Asn Thr Arg Val Gly Arg Ser Val Val Ala Asn Tyr Asp Gln
35 40 45

Met Met Arg Val Pro Ile Gln Arg Arg Ala Lys Val Met Ser Ile Arg
50 55 60

Gly Glu Arg Ser Tyr Asn Thr Pro Leu Gly Lys Val Ala Met Lys Asn
65 70 75 80

Gly Leu Ser Asp Lys Asp Met Lys Asp Val Ser Ala Asp Leu Val Ile

```
                          85                  90                  95
Ser Thr Val Thr Ala Pro Arg Thr Asp Pro Ala Gly Thr Gly Ala Glu
                100                 105                 110

Asn Ser Asn Met Thr Leu Lys Ile Leu Asn Asn Thr Gly Val Asp Leu
            115                 120                 125

Leu Ile Asn Asp Ile Thr Val Arg Pro Thr Val Ile Ala Gly Asn Ile
        130                 135                 140

Lys Gly Asn Thr Met Ser Asn Thr Tyr Phe Ser Ser Lys Asp Ile Lys
145                 150                 155                 160

Ser Ser Ser Ser Lys Ile Thr Leu Ile Asp Val Cys Ser Lys Phe Glu
                165                 170                 175

Asp Gly Ala Ala Phe Glu Ala Thr Met Asn Ile Gly Phe Thr Ser Lys
            180                 185                 190

Asn Val Ile Asp Ile Lys Asp Glu Ile Lys Lys Lys
        195                 200
```

<210> SEQ ID NO 11
<211> LENGTH: 627
<212> TYPE: DNA
<213> ORGANISM: white spot syndrome baculovirus

<400> SEQUENCE: 11

```
atgcacatgt gggggggttta cgccgctata ctggcgggtt tgacattgat actcgtggtt      60
atatctatag ttgtaaccaa catagaactt aacaagaaat ggacaagaa ggataaagac       120
gcctaccctg ttgaatctga ataataaac ttgaccatta acggtgttgc tagaggaaac       180
cactttaact ttgtaaacgg cacattacaa accaggaact atggaaaggt atatgtagct      240
ggccaaggaa cgtccgattc tgaactggta aaaagaaag gagacataat cctcacatct       300
ttacttggag acggagacca cacactaat gtaaacaaag ccgaatctaa agaattagaa       360
ttgtatgcaa gagtatacaa taatacaaag agggatataa cagtggactc tgtttcactg      420
tctccaggtc taaatgctac aggaagggaa ttttcagcta caaatttgt attatatttc       480
aaaccaacag ttttgaagaa aataggatc aacacacttg tgtttggagc aacgtttgac       540
gaagacatcg atgatacaaa taggcattat ctgttaagta tgcgattttc tcctggcaat      600
gatctgttta aggttgggga aaaataa                                          627
```

<210> SEQ ID NO 12
<211> LENGTH: 208
<212> TYPE: PRT
<213> ORGANISM: white spot syndrome baculovirus

<400> SEQUENCE: 12

```
Met His Met Trp Gly Val Tyr Ala Ala Ile Leu Ala Gly Leu Thr Leu
1               5                   10                  15

Ile Leu Val Val Ile Ser Ile Val Thr Asn Ile Glu Leu Asn Lys
            20                  25                  30

Lys Leu Asp Lys Lys Asp Lys Asp Ala Tyr Pro Val Glu Ser Glu Ile
        35                  40                  45

Ile Asn Leu Thr Ile Asn Gly Val Ala Arg Gly Asn His Phe Asn Phe
    50                  55                  60

Val Asn Gly Thr Leu Gln Thr Arg Asn Tyr Gly Lys Val Tyr Val Ala
65                  70                  75                  80

Gly Gln Gly Thr Ser Asp Ser Glu Leu Val Lys Lys Gly Asp Ile
                85                  90                  95
```

```
Ile Leu Thr Ser Leu Leu Gly Asp Gly Asp His Thr Leu Asn Val Asn
            100                 105                 110

Lys Ala Glu Ser Lys Glu Leu Glu Leu Tyr Ala Arg Val Tyr Asn Asn
            115                 120                 125

Thr Lys Arg Asp Ile Thr Val Asp Ser Val Ser Leu Ser Pro Gly Leu
        130                 135                 140

Asn Ala Thr Gly Arg Glu Phe Ser Ala Asn Lys Phe Val Leu Tyr Phe
145                 150                 155                 160

Lys Pro Thr Val Leu Lys Lys Asn Arg Ile Asn Thr Leu Val Phe Gly
                165                 170                 175

Ala Thr Phe Asp Glu Asp Ile Asp Asp Thr Asn Arg His Tyr Leu Leu
            180                 185                 190

Ser Met Arg Phe Ser Pro Gly Asn Asp Leu Phe Lys Val Gly Glu Lys
            195                 200                 205

<210> SEQ ID NO 13
<211> LENGTH: 25
<212> TYPE: DNA
<213> ORGANISM: Artificial
<220> FEATURE:
<223> OTHER INFORMATION: Probe or primer
<220> FEATURE:
<221> NAME/KEY: misc_feature
<222> LOCATION: (23)..(23)
<223> OTHER INFORMATION: n is a, c, g, or t

<400> SEQUENCE: 13
cagaattcat gcayatgtgg ggngt                                    25

<210> SEQ ID NO 14
<211> LENGTH: 29
<212> TYPE: DNA
<213> ORGANISM: Artificial
<220> FEATURE:
<223> OTHER INFORMATION: Probe or primer
<220> FEATURE:
<221> NAME/KEY: misc_feature
<222> LOCATION: (24)..(24)
<223> OTHER INFORMATION: n is a, c, g, or t

<400> SEQUENCE: 14
cagaattcyt trtcyttytt rtcnarytt                                29
```